US007122312B1

(12) United States Patent
Friend et al.

(10) Patent No.: US 7,122,312 B1
(45) Date of Patent: Oct. 17, 2006

(54) METHODS FOR DRUG TARGET SCREENING

(75) Inventors: Stephen H. Friend, Seattle, WA (US); Leland Hartwell, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 326 days.

(21) Appl. No.: 10/232,211

(22) Filed: Aug. 30, 2002

Related U.S. Application Data

(62) Division of application No. 09/031,216, filed on Feb. 26, 1998, now Pat. No. 6,165,709.

(60) Provisional application No. 60/039,134, filed on Feb. 28, 1997, provisional application No. 60/056,109, filed on Aug. 20, 1997.

(51) Int. Cl.
*C12Q 1/68* (2006.01)
(52) U.S. Cl. .......................................... 435/6; 435/463
(58) Field of Classification Search ..................... 435/6
See application file for complete search history.

(56) References Cited

U.S. PATENT DOCUMENTS

| | | | |
|---|---|---|---|
| 5,445,934 A | 8/1995 | Fodor et al. | |
| 5,569,588 A | 10/1996 | Ashby et al. | |
| 5,645,988 A | 7/1997 | Vande Woude et al. | |
| 5,744,305 A | 4/1998 | Fodor et al. | |
| 5,777,888 A | 7/1998 | Rine et al. | |
| 5,800,992 A | 9/1998 | Fodor et al. | |
| 5,811,231 A | 9/1998 | Farr et al. | |
| 5,886,162 A * | 3/1999 | Kalman | 536/22.1 |
| 6,333,155 B1 | 12/2001 | Lockhart et al. | |

FOREIGN PATENT DOCUMENTS

| | | |
|---|---|---|
| EP | 0 816 511 A1 | 1/1996 |
| WO | WO 94/17208 | 8/1994 |
| WO | WO 95/11969 | 5/1995 |
| WO | WO 96/23075 | 8/1996 |
| WO | WO 97/10365 | 3/1997 |
| WO | WO 97/27317 | 7/1997 |
| WO | WO 97/48822 | 12/1997 |
| WO | WO 98/06874 | 2/1998 |

OTHER PUBLICATIONS

Watson et al. Yeast as the *E. coli* of eukaryotic cells. In Molecular Biology of the Gene, vol. 1, pp. 550-594. 1987.*
U.S. Appl. No. 09/074,983, filed May 8, 1998, Stoughton and Friend.
U.S. Appl. No. 09/099,722, filed Jun. 19, 1998, Stoughton and Karp.
U.S. Appl. No. 60/084,742, filed May 8, 1998, Friend and Stoughton.
U.S. Appl. No. 60/090,004, filed Jun. 19, 1998, Friend and Stoughton.
U.S. Appl. No. 60/090,046, filed Jun. 19, 1998, Friend and Stoughton.

U.S. Appl. No. 60/092,512, filed Jul. 13, 1998, Friend et al.
Anderson et al., 1994, "Involvement of the protein tyrosine kinase p56$^{lck}$ in T cell signalling and thymocyte development", Adv. Immunol. 56:151-178.
Baudin et al., 1993, "A simple and efficient method for direct gene deletion in *Saccharomyces cerevisiae*", Nucl. Acids Res. 21:3329-3330.
Belshaw et al., 1996, "Controlling protein association and subcellular localization with a synthetic ligand that induces heterodimerization of proteins", Proc. Natl. Acad. Sci. USA 93:4604-4607.
Biocca, 1995, "Intracellular immunization: antibody targeting to subcellular compartments", Trends in Cell Biology 5:248-253.
Blanchard et al., 1996, "Sequence to array: probing the genome's secrets", Nature Biotechnology 14:1649.
Blanchard et al., 1996, "High-density oligonucleotide arrays", Biosensors & Bioelectronics 11:687-690.
Chee et al., 1996, "Accessing genetic information with high-density DNA arrays", Science 274:610-614.
Cotten and Birnsteil, 1989, "Ribozyme mediated destruction of RNA in vivo", EMBO J. 8:3861-3866.
Dohmen et al., 1994, "Heat-inducible degron: a method for constructing temperature-sensitive mutants", Science 263: 1273-1276.
Gari et al., 1997, " A set of vectors with a tetracycline-regulatable promoter system for modulated gene expression in *Saccharomyces crevisiae*", Yeast 13:837-848.
Goffreau et al., 1996, "Life with 6000 genes", Science 274:546-567.
Gossen and Bujard, 1992, "Tight control of gene expression in mammalian cells by tetracycline-responsive promoters", Proc. Natl. Acad. Sci, USA 89:5547-5551.
Gossen et al., 1995, "Transcriptional activation by tetracyclines in mammalian cells" Science 268:1766-1769.
Guo et al., 1994, "Direct fluorescence analysis of genetic polymorphisms by hybridization with oligonucleotide arrays on glass supports", Nucl. Acids Res. 22:5456-5465.
Hanke et al., 1996, "Discovery of a novel, potent, and Src family-selective tyrosine kinase inhibitor", J. Biol. Chem. 271:695-701.

(Continued)

*Primary Examiner*—James Ketter
(74) *Attorney, Agent, or Firm*—Jones Day

(57) ABSTRACT

The present invention provides methods for identifying targets of a drug in a cell by comparing (i) the effects of the drug on a wild-type cell, (ii) the effects on a wild-type cell of modifications to a putative target of the drug, and (iii) the effects of the drug on a wild-type cell which has had the putative target modified of the drug. In various embodiments, the effects on the cell can be determined by measuring gene expression, protein abundances, protein activities, or a combination of such measurements. In various embodiments, modifications to a putative target in the cell can be made by modifications to the genes encoding the target, modification to abundances of RNAs encoding the target, modifications to abundances of target proteins, or modifications to activities of the target proteins. The present invention also provides methods for drug development based on the methods for identifying drug targets.

27 Claims, 8 Drawing Sheets

OTHER PUBLICATIONS

Hartwell et al., 1997, "Integrating genetic approaches into the discovery of anticancer drugs", Science 278:1064-1068.
Hayden et al., 1997, "Antibody engineering", Curr. Opin. Immunol. 9:201-212.
Herskowitz, 1987, "Functional inactivation of genes by dominant negative mutations", Nature 329:219-222.
Hoffmann et al., 1997, "A novel tetracycline-dependent expression vector with low basal expression and potent regulatory properties in various mammalian cell lines" Nucl. Acids Res. 25:1078-1079.
Johnson and Davis, 1984, "Sequences that regulate the divergent GAL1-GAL10 promoter in Saccharomyces cerevisiae", Mol. Cell. Biol. 4:1440-1448.
Kerjan et al., 1986, "Nucleotide sequence of Saccharomyces cerevisiae MET25 gene", Nucl. Acids Res. 14:7861-7871.
Lander, 1996, "The new genomics: Global views of biology", Science 274:536-539.
Lennon and Lehrach, 1991, "Hybridization analyses of arrayed cDNA libraries" TIG 7:314-317.
Mascorro-Gallardo et al., 1996, "Construction of a CUP1 promoter-based vector to modulate gene expression in Saccharomyces cerevisiae", Gene 172:169-170.
Matheos et al., 1997, "Ten1p/Crz1p, a calcineurin-dependent transcription factor that differentially regulates gene expression in Saccharomyces cerevisiae", Genes & Dev. 11:3445-3458.
McAdams and Shapiro, 1995, "Circuit simulation of genetic networks", Science 269:650-656.
Mikulecky, 1990, "Modeling intestinal absorption and other nutrition-related processes using PSPICE and STELLA", J. Ped. Gastroenterol. Nutr. 11:7-20.
Mounts and Liebman, 1997, "Quantitative modeling of normal blood coagulation an its pathological states using stochastic activity networks", Int. J. Biol. Macromolecules 20:265-281.
Murmberg et al., 1994, "Regulatable promoters of Saccharomyces cerevisiae: Comparison of transcriptional activity and their use for heterologous expression", Nucl. Acids Res. 22:5767-5768.
Nguyen et al., 1995, "Differential gene expression in the murine thymus assayed by quantitative hybridization of arrayed cDNA clones", Genomics 29:207-216.
No et al., 1996, "Ecdysone-inducible gene expression in mammalian cells and Transgenic mice", Proc. Natl. Acad. Sci. USA 93:3346-3351.
Nocka et al., 1990, "Molecular bases of dominant negative and loss of function mutations at the murine c-kit/white spotting locus: $W_{37}$, $W^v$, $W^{41}$ and W", EMBO J. 9:1805-1813.
Oliff and Friend, 1997, "Cancer, principles & practice of oncology, molecular targets for drug development", Mol. Pharmacol. 68:3115-3125.
Perlmuttr and Alberola-Ila, 1996, "The use of dominant-negative mutations to elucidate signal transduction pathways in lymphocytes", Curr. Opin. Immunol. 8:285-290.
Polyak et al., 1997, "A model for p53-induced apoptosis", Nature 389:300-306.
Reinitz and Sharp, 1995, "Mechanism of eve stripe formation", Mech. Dev. 49:133-158.

Schena, 1996, "Genome analysis with gene expression microarrays", BioEssays 18:427.
Schena et al., 1996, "Parallel human genome analysis: microarray-based expression monitoring of 1000 genes", Proc. Natl. Acad. Sci. USA 93:10614-10619.
Schena et al., 1995, "Quantitative monitoring of gene expression patterns with a complementary DNA microarray", Science 270:467-470.
Shalon et al., 1996, "A DNA microarray system for analyzing complex DNA samples using two-color fluorescent probe hybridization", Genome Research 639-645.
Shiue, 1997, "Identification of candidate genes for drug discovery by differential display", Drug Dev. Res. 41:142-159.
Shoemaker et al., 1996, "Quantitative phenotypic analysis of yeast deletion mutants using a highly parallel molecular bar-coding strategy", Nature Genetics 14:450-456.
Southern, 1996, "DNA chips: analysing sequence by hybridization to oligonucleotides on a large scale", TIG 12:110-115.
Spencer, 1996, "Creating conditional mutations in mammals", TIG 12:181-187.
Stathopoulos and Cyert,,, 1997, "Calcineurin acts through the CRZ1/TCN1-encoded transcription factor to regulate gene expression in yeast", Genes & Dev. 11:3432-3444.
Straus and Weiss, 1992, "Genetic evidence for the involvement of the lck tyrosine kinase in signal transduction through the T cell antigen receptor", Cell 70:585-593.
Thomas et al., 1995, "Dynamical behaviour of biological regulatory networks—I. Biological role of feedback loops and practical use of the concept of the loop-characteristic state", Bull. Math. Biol. 57:247-276.
Yuh et al., 1998, "Genomic Cis-regulatory logic: experimental and computational analysis of a sea urchin gene", Science 279:1896-1902.
Velculescu et al., 1995, "Serial analysis gene expression", Science 270:484-487.
Zhao et al., 1995, "High-density cDNA filter analysis: a novel approach for large-scale, quantitative analysis of gene expression", Gene 156:207-213.
Weinstein et al., "An Information-Intensive Approach to the Molecular Pharmacology of Cancer," Science vol. 275, pp. 343-349 (Jan. 17, 1997)—(from Suppl. IDS)—.
Wang et al., 1996, "Rapamycin Inhibits Aldolase A Expression During Human Lymphocyte Activation", Journal of Cellular Biochemistry 63:239-251.
Schreiber et al., 1997, "Immunophilins, Ligands, and the Control of Signal Transduction", The Harvey Lectures, Series 91, pp. 99-114.
Agrawal, S., 1996, "Antisense Oligonucleotides: towards clinical trials", Trends in Biotechnology, 14:376-387 (abstract).
Marton et al., 1998, "Drug target validation and identification of secondary drug target effects using DNA microarrays", Nature Medicine, 4:1293-1301.
Supplementary European Search Report dated Jul. 15, 2004 for European Application No. EP 98 91 0093.

* cited by examiner

WILDTYPE DRUG
TRANSCRIPT ARRAY

COMPENDIUM OF MUTANT TRANSCRIPT ARRAYS

MUTANT Δ1 DRUG
TRANSCRIPT ARRAY

MUTANT Δ1 DRUG    WILDTYPE DRUG
TRANSCRIPT ARRAY   TRANSCRIPT ARRAY

REMAINS   DROPS OUT

MUTANT Δ2 DRUG
TRANSCRIPT ARRAY

MUTANT Δ2 DRUG          WILDTYPE DRUG
TRANSCRIPT ARRAY        TRANSCRIPT ARRAY

VS.

REMAINS          DROPS OUT

MUTANT Δ7 DRUG
TRANSCRIPT ARRAY

METHODS FOR DRUG TARGET SCREENING

This application is a division of application Ser. No. 09/031,216, filed Feb. 26, 1998 (now U.S. Pat. No. 6,165,709), which is incorporated herein by reference in its entirety for all purposes.

The application claims benefit of now abandoned U.S. Provisional Patent Applications Ser. No. 60/039,134, filed on Feb. 28, 1997, and Ser. No. 60/056,109, filed on Aug. 20, 1997, both of which are hereby incorporated by reference in their entireties.

1 FIELD OF THE INVENTION

The field of this invention relates to methods for characterizing the action of drugs in cells, in particular for finding direct targets of drugs, as well as application of these methods to drug discovery.

2 BACKGROUND

Drug discovery, a process by which bioactive compounds are identified and preliminarily characterized, is a critical step in the development of treatments for human diseases. Two approaches presently dominate the search for new drugs. The first begins with a screen for compounds that have a desired effect on a cell (e.g., induction of apoptosis), or organism (e.g., inhibition of angiogenesis) as measured in a specific assay. Compounds with the desired activity may then be modified to increase potency, stability, or other properties, and the modified compounds retested in the assay. Thus, a compound that acts as an inhibitor of angiogenesis when tested in a mouse tumor model may be identified, and structurally related compounds synthesized and tested in the same assay. One limitation of this approach is that, often, the mechanism of action and molecular target(s) affected by the compound are unknown, and cannot be determined by the screen. In addition, the assay may provide little information about the specificity of the drug's effect. Finally, the number of compounds that can be screened by assaying biological effects on cells or animals is limited.

In contrast, the second approach to drug screening involves testing numerous compounds for a specific effect on a known molecular target, typically a cloned gene sequence or an isolated enzyme or protein. For example, high-throughput assays can be developed in which numerous compounds can be tested for the ability to change the level of transcription from a specific promoter or the binding of identified proteins. Although the use of high-throughput screens is an extremely powerful methodology for identifying drug candidates, it has limitations. A major drawback is that the assay provides little or no information about the effects of a compound at the cellular or organismal level. These effects must be tested by using the drug in a series of cell biologic and whole animal studies to determine toxicity or side effects in vivo. In fact, analysis of the specificity and toxicity studies of candidate drugs can consume a significant fraction of the drug development process (see, e.g., Oliff, A and S. H. Friend, "Molecular Targets for Drug Development," in DeVita et al. *Cancer: Principles & Practice of Oncology* 5th Ed. 1997 Lippincott-Raven Publishers, Philadelphia).

Further, raw data from gene expression analysis are often difficult to coherently interpret. Such measurement technologies typically return numerous genes with altered expression in response to a drug, typically 50–100, possibly up to 1,000 or as few as 10. In the typical case, without more analysis, it is not possible to discern cause and effect from such data alone. The fact that one gene among many has an altered expression in a pair of related biological states yields little or no insight into what caused this change and what the effects of this change are. One is left to ad hoc further experimentation to interpret such gene expression results in terms of biological mechanism. Systematic procedures for guiding the interpretation of such data and such further experimentation, at least in the case of drug target screening, are needed.

Thus, there is a need for improved (e.g., faster and less expensive) methods for characterizing activities and targets of drugs based on effective interpretation of expression data. The present invention provides methods for rapidly characterizing the specificity of candidate drugs and identifying their molecular targets.

3 SUMMARY OF THE INVENTION

The present invention provides methods for identifying targets of a drug in a cell by comparing (i) the effects of the drug on a wild-type cell, (ii) the effects on a wild-type cell of modifications to a putative target of the drug, and (iii) the effects of the drug on a wild-type cell which has had the putative target modified. In various embodiments, the effects on the cell can be determined by measuring gene expression, protein abundances, protein activities, or a combination of such measurements. In various embodiments, modifications to a putative target in the cell can be made by modifications to the genes encoding the target, modification to abundances of RNAs encoding the target, modifications to abundances of target proteins, or modifications to activities of the target proteins. The present invention also provides methods for drug development based on the methods for identifying drug targets.

Accordingly, in a first embodiment, this invention provides a method of determining that a specific cellular constituent present in a cell type is a target of a drug, said method comprising: (a) identifying cellular constituents as perturbed or as not perturbed in a cell of said cell type that is exposed to said drug in comparison to a cell of said cell type that is not exposed to said drug; (b) identifying cellular constituents as perturbed or as not perturbed in a cell of said cell type that both is exposed to said drug and also has said specific cellular constituent modified in comparison to a cell of said cell type that has said specific cellular constituent modified and is not exposed to said drug; (c) identifying cellular constituents that drop out by a method comprising determining each of said cellular constituents that is both identified in step (a) as perturbed and that is also identified in step (b) as either differently perturbed or not perturbed; and (d) ascertaining if each said cellular constituent identified in step (c) to drop out is also identified as perturbed in a cell of said cell type that has said specific cellular constituent modified in comparison to a cell of said cell type that does not have said specific cellular constituent modified, whereby said specific cellular constituent is determined as a target of said drug.

In one aspect of the first embodiment, this invention further provides that said ascertaining step further comprises ascertaining if each said cellular constituent that is identified in step (c) to drop out and is identified as perturbed in said ascertaining step is also identified as similarly perturbed in step (a). In a second aspect of the first embodiment, this invention further provides that step (c) further comprises excluding said specific cellular constituent from said cellular constituents identified to drop out, and wherein step (d) further comprises excluding said specific cellular constituent from said cellular constituents identified as perturbed.

In a second embodiment, this invention provides a method of determining that a specific gene (or genes) or a product of a specific gene (or products of specific genes) present in a cell type is a target of a drug, said method comprising: (a) identifying genes whose expression is perturbed or is not perturbed in a cell of said cell type that is also exposed to said drug in comparison to a cell of said cell type that is not exposed to said drug, by a method comprising contacting (e.g., hybridizing) one or more gene transcript arrays with (i) RNA from said cell, or cDNA derived therefrom, exposed to said drug and with (ii) RNA from said cell, or cDNA derived therefrom, not exposed to said drug, wherein said gene transcript array comprises a surface with attached nucleic acids or nucleic acid mimics, said nucleic acids or nucleic acid mimics being capable of hybridizing with RNA species present in said cell type or with cDNA species synthesized from said RNA species; (b) identifying genes whose expression is perturbed or is not perturbed in a cell of said cell type that both is exposed to said drug and also has said specific gene modified in comparison to a cell of said cell type that has said specific gene modified and is not exposed to said drug, by a method comprising contacting one or more gene transcript arrays with (i) RNA from said cell, or cDNA derived therefrom, exposed to said drug and having said specific gene modified and with (ii) RNA from said cell, or cDNA derived therefrom, having said specific gene modified and not exposed to said drug; (c) identifying genes that drop out by a method comprising determining each of said genes that is both identified in step (a) as perturbed and that is also identified in step (b) as either differently perturbed or not perturbed; and (d) ascertaining if each said gene identified in step (c) to drop out is also identified as a gene whose expression is perturbed in a cell of said cell type that has said specific gene modified in comparison to a cell of said cell type that does not have said specific gene modified by a method comprising contacting one or more gene transcript arrays with (i) RNA from said cell, or cDNA derived therefrom, having said specific gene modified and with (ii) RNA from said cell, or cDNA derived therefrom, not having said specific gene modified, whereby said specific gene is determined as a target of said drug.

In one aspect of the second embodiment, this invention further provides that said ascertaining step further comprises ascertaining if each said gene that is identified in step (c) to drop out and is identified as perturbed in said ascertaining step is also identified as similarly perturbed in step (a). In a second aspect of the second embodiment, this invention further provides that step (c) further comprises excluding said specific gene from said genes identified to drop out, and wherein step (d) further comprises excluding said specific gene from said genes identified as perturbed.

In a third embodiment, this invention provides a method of determining one or more drug targets in a cell type comprising: (a) identifying cellular constituents as perturbed or as not perturbed in a cell of said cell type that is exposed to said drug in comparison to a cell of said cell type that is not exposed to said drug; (b) identifying a specific cellular constituent as a potential drug target if at least one cellular constituent identified in step (a) as perturbed is also identified as similarly perturbed in a cell of said cell type that has said potential drug target modified in comparison to a cell of said cell type that does not have said potential drug target modified; (c) identifying cellular constituents as perturbed or as not perturbed in a cell of said cell type that both is exposed to said drug and also has said potential drug target modified in comparison to a cell of said cell type that has said potential drug target modified and is not exposed to said drug; (d) identifying cellular constituents that drop out by a method comprising determining each of said cellular constituents that is both identified in step (a) as perturbed and that is also identified in step (c) as either differently perturbed or not perturbed; and (e) ascertaining if each said cellular constituent identified to drop out in step (d) is also identified in step (b) as perturbed, whereby said potential drug target is determined as a drug target.

In one aspect of the third embodiment, this invention further provides for repeating steps (b), (c), (d), and (e) with a different specific cellular constituent modified until all cellular constituents identified in step (a) as perturbed have been identified in step (d) to drop out from modification of at least one of said one or more determined drug targets. In a second aspect of the third embodiment, this invention further provides that perturbation values are identified for said cellular constituents identified as perturbed, and that said ascertaining step further comprises ascertaining, for each cellular constituent identified in step (d) to drop out due to modification of at least two of said one or more determined drug targets, if a combination of perturbation values identified for said cellular constituent in step (b) due to modification of said at least two of said one or more determined drug targets is similar to said perturbation value identified for said cellular constituent in step (a). In a third aspect of the third embodiment, this invention further provides that the combination of perturbation values is preformed by a method comprising adding perturbation values.

In a fourth embodiment, this invention provides a method of determining one or more drug targets in a cell type comprising: (a) performing for each of a plurality of pre-determined cellular constituents, a method comprising identifying cellular constituents as perturbed or as not perturbed in a cell of said cell type that has modified a cellular constituent selected from among said plurality of pre-determined cellular constituents in comparison to a cell of said cell type that does not have said selected cellular constituent modified; (b) identifying cellular constituents as perturbed or as not perturbed in a cell of said cell type that is exposed to said drug in comparison to a cell of said cell type that is not exposed to said drug; (c) determining a specific cellular constituent selected from among said plurality of pre-determined cellular constituents as a potential drug target if at least one cellular constituent identified in step (a) as perturbed when said specific cellular constituent is modified is also identified in step (b) as similarly perturbed; (d) identifying cellular constituents as perturbed or as not perturbed in a cell of said cell type that both is exposed to said drug and also has said potential drug target modified in comparison to a cell of said cell type that has said potential drug target modified and is not exposed to said drug; (e) identifying cellular constituents that drop out by a method comprising determining each of said cellular constituents that is both identified in step (b) as perturbed and that is also identified in step (d) as either differently perturbed or not perturbed; and (f) ascertaining if each said cellular constituent identified in step (e) to drop out is also identified in step (a) as perturbed when said potential drug target is modified, whereby said potential drug target is determined as a drug target.

In one aspect of the fourth embodiment, this invention further provides that said potential drug target is determined as one specific cellular constituent selected from said plurality of pre-determined cellular constituents for which the greatest number of cellular constituents that are identified in step (a) as perturbed when said specific cellular constituent is modified are also identified in step (b) as similarly perturbed.

In a fifth embodiment, this invention provides a method of determining that a putative drug target is an actual drug target comprising: (a) identifying cellular constituents as perturbed or as not perturbed in a cell of said cell type that is exposed to said drug in comparison to a cell of said cell type that is not exposed to said drug; (b) identifying cellular constituents as perturbed or as not perturbed in a cell of said cell type that has said putative drug target modified in comparison to a cell of said cell type that does not have said putative drug target modified; and (c) ascertaining if each said cellular constituent identified as perturbed in step (a) is also identified as perturbed in step (b), whereby said putative drug target is determined as an actual drug target.

In a sixth embodiment, this invention provides a method of determining a more target-specific drug candidate from an initial drug candidate comprising: (a) determining targets of an initial drug candidate by the method of any of the first through the fifth embodiments: (b) modifying the structure of said initial drug candidate; (c) determining targets of said modified initial drug candidate by the method of any of the first through the fifth embodiments; and (d) determining that said modified initial drug candidate is a more target-specific drug candidate than said initial drug candidate if said modified initial drug candidate has fewer targets than said initial drug candidate.

In a seventh embodiment, this invention provides a method of identifying one or more specific cellular constituents present in a cell type that are targets of a drug and that mediate side-effects of the drug, said method comprising: (a) carrying out the method of any of the first through the fifth embodiments for a first drug; (b) carrying out the method of any of the first through the fifth embodiments for a second drug, wherein the first and the second drug are different and exhibit therapeutic efficacy for the same disease or disorder; and (c) identifying those specific cellular constituents determined to be targets of said first drug that are different from those specific cellular constituents determined to be targets of said second drug, thereby identifying one or more specific cellular constituents present in a cell type that are targets of said first drug that mediate side-effects of said first drug.

In an eighth embodiment, this invention provides a method of identifying one or more specific cellular constituents present in a cell type that are targets mediating therapeutic efficacy for a disease or disorder, said method comprising: (a) carrying out the method of any of the first through the fifth embodiments for a first drug; (b) carrying out the method of any of the first through the fifth embodiments for a second drug, wherein the first and the second drug are different and exhibit therapeutic efficacy for the same disease or disorder; and (c) identifying those specific cellular constituents determined to be targets of both said first drug and said second drug, thereby identifying one or more specific cellular constituents present in a cell type that are targets of said first drug that mediate therapeutic efficacy for said disease or disorder.

In a ninth embodiment, this invention provides a method of determining that a specific cellular constituent present in a cell type is a target of a change in the cellular environment, said method comprising: (a) identifying cellular constituents as perturbed or as not perturbed in a cell of said cell type that is exposed to said change in the cellular environment in comparison to a cell of said cell type that is not exposed to said change in the cellular environment; (b) identifying cellular constituents as perturbed or as not perturbed in a cell of said cell type that both is exposed to said change in the cellular environment and also has said specific cellular constituent modified in comparison to a cell of said cell type that has said specific cellular constituent modified and is not exposed to said change in the cellular environment; (c) identifying cellular constituents that drop out by a method comprising determining each of said cellular constituents that is both identified in step (a) as perturbed and that is also identified in step (b) as either differently perturbed or not perturbed; and (d) ascertaining if each said cellular constituent identified in step (c) to drop out is also identified as perturbed in a cell of said cell type that has said specific cellular constituent modified in comparison to a cell of said cell type that does not have said specific cellular constituent modified, whereby said specific cellular constituent is determined as a target of said change in the cellular environment.

4 BRIEF DESCRIPTION OF THE DRAWINGS

FIG. 1 illustrates the use of deletion mutants in analysis of a drug. FIG. 1A shows an illustrative four-element gene network. FIG. 1B shows the mutant transcript array resulting when a drug that inhibits gene B or which activates gene D is administered. FIG. 1C shows that these two drug activities can be distinguished when deletion mutants (mutant drug transcript arrays) are used.

Figure 3A:
FIG. 3 shows a schematic representation of results described in Example 6.5.
Figure 3B:
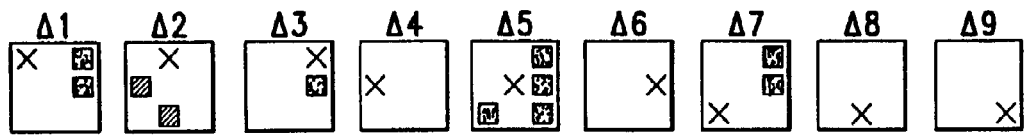
Figure 3C:
Figure 3D:
Figure 3E:
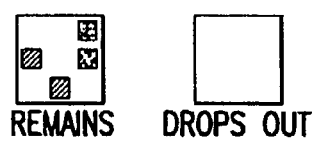
Figure 3F:
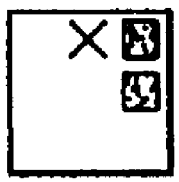
Figure 3G:
Figure 3G:
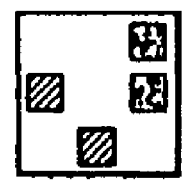
Figure 3H:
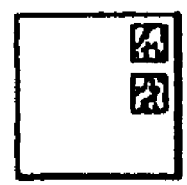
Figure 3H:
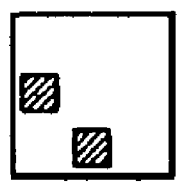
Figure 3I:
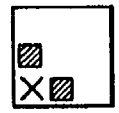
Figure 3J:
Figure 3K:
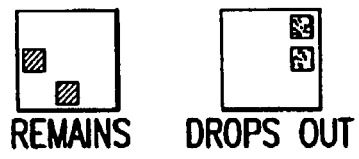
Figure 3L:
Figures 4A, 4B, 4C:
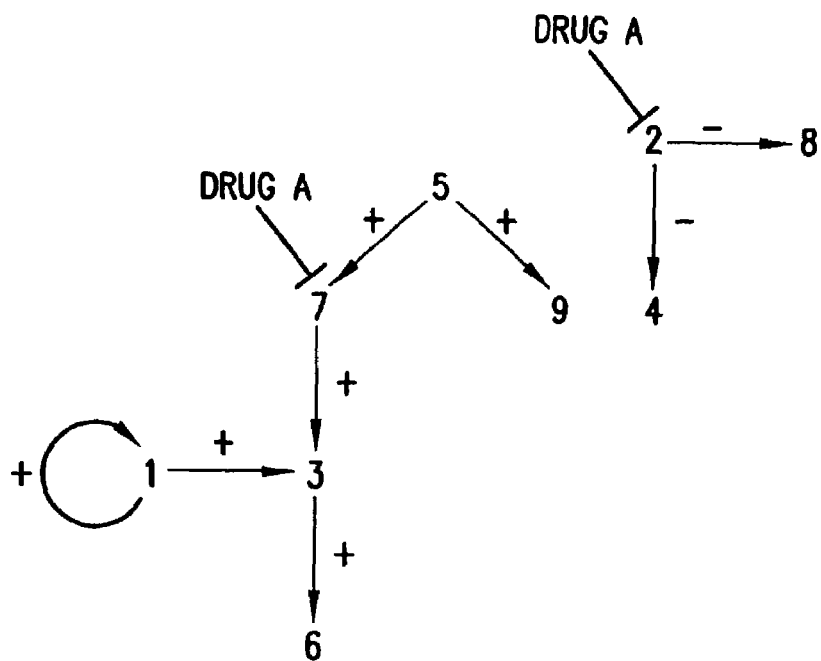

FIG. 4 provides keys for interpreting FIG. 3. FIG. 4A shows the numbering system for the schematic transcript arrays of the examples. FIG. 4B shows the symbols used to describe perturbations. FIG. 4C shows a gene interaction that accounts for the results of Example 6.5.

Figure 5:
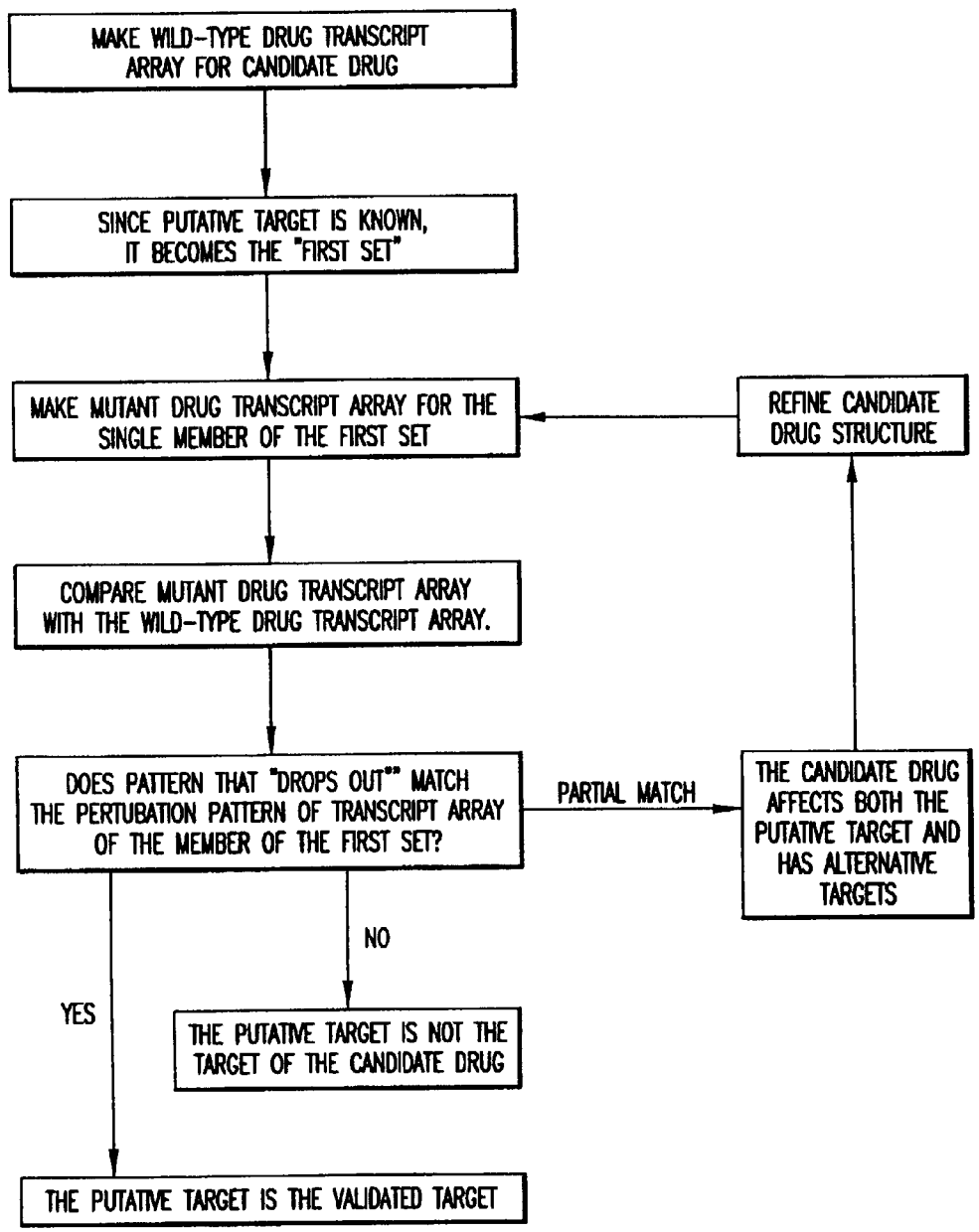

FIG. 5 is flow-chart summarizing steps in a method of identifying a drug target.

Figure 6:
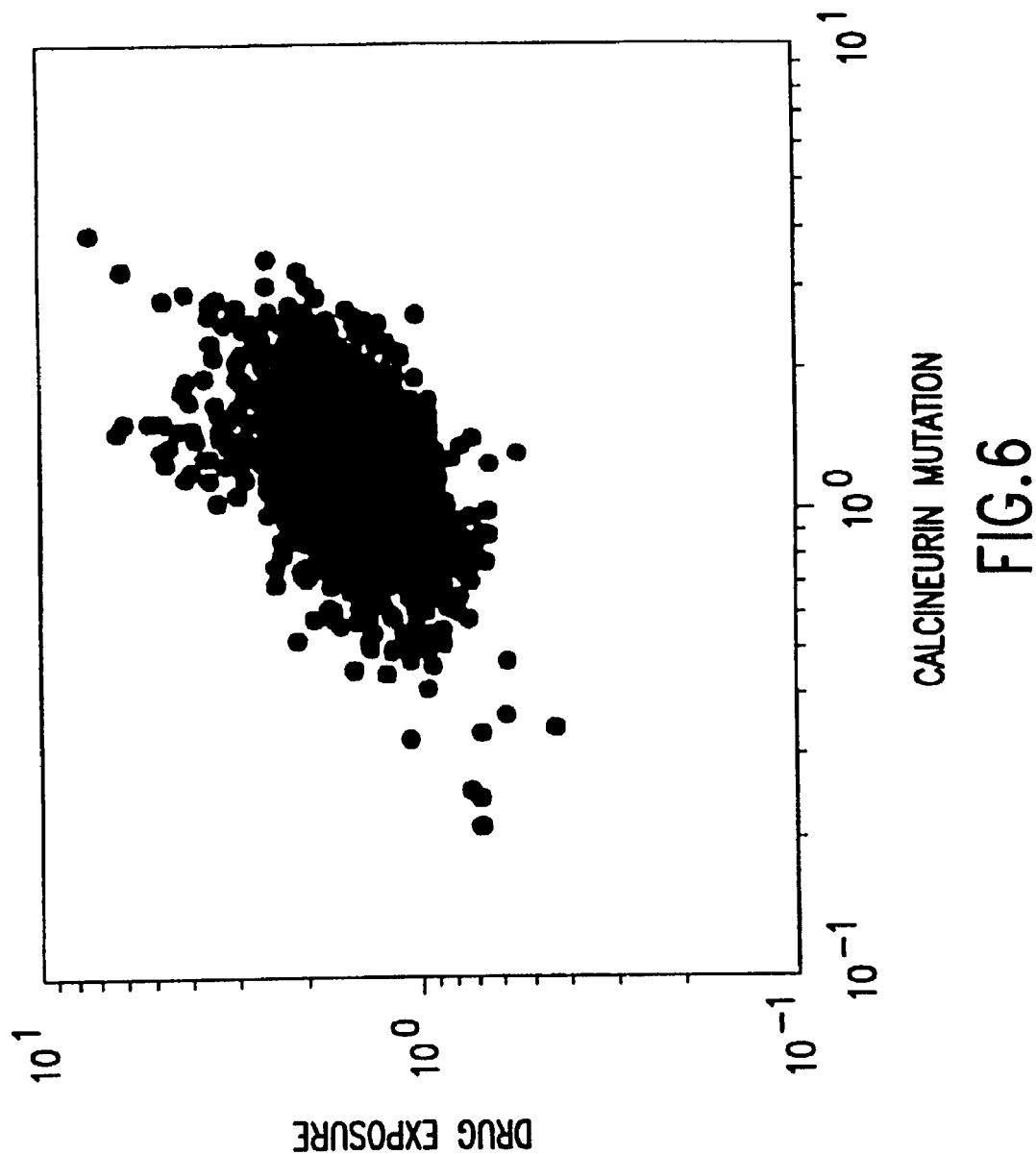

FIG. 6 illustrates a graphical representation of the similarity between the wild-type cyclosporin A ("CSA") drug transcript array and the calcineurin ("cna") deletion mutant transcript array. The logarithm of the expression ratios for substantially all the ORFs in the S. cerevisiae genome were plotted on the X axis (for cna deletion mutant transcript array) and Y axes (for the wild-type CSA transcript array). Genes which were perturbed in the same way (activated, inhibited, or unaffected) to the same extent in both experiments are expected to fall on the diagonal X=Y.

DETAILED DESCRIPTION

This section presents a detailed description of the invention and its application to drug screening. This description is by way of several exemplary illustrations, in increasing detail and specificity, of the general methods of this invention. These examples are non-limiting, and related variants that will be apparent to one of skill in the art are intended to be encompassed by the appended claims. Following these examples are descriptions of embodiments of the data gathering steps that accompany the general methods. First, embodiments for measuring various aspects of the biological state of a cell are described, followed by descriptions of embodiments for controlled and targeted modification of the biological state of cell. It is understood that in particular embodiments, this invention can combine any of the embodiments of the general methods of this invention, along with any of the embodiments for measuring the biological state of a cell, and along with any of the embodiments for targeted modification of the biological state of a cell.

5.1 Introduction

This section, first, presents concepts and definitions relating to drug activity, which are generally useful in describing this invention, and second, presents a general and non-limiting overview of the general methods of this invention.

Drug Activity

The present invention provides methods for characterizing the effects on a biological system (e.g., a cell or a patient) of known or novel drugs or drug candidates, and can be used for, among other uses, drug screening, including characterizing drug targets and improvement of lead compounds. This subsection reviews drug activity in general and defines several terms used herein to describe drug activity.

As used herein, drugs are any compounds of any degree of complexity that perturb a biological system, whether by known or unknown mechanisms and whether or not they are used therapeutically. Drugs thus include: typical small molecules of research or therapeutic interest; naturally-occurring factors, such as endocrine, paracrine, or autocrine factors or factors interacting with cell receptors of all types; intracellular factors, such as elements of intracellular signaling pathways; factors isolated from other natural sources; and so forth. The biological effect of a drug may be a consequence of, inter alia, drug-mediated changes in the rate of transcription or degradation of one or more species of RNA, the rate or extent of translation or post-translational processing of a polypeptide, the rate or extent of protein degradation, the inhibition or stimulation of protein action or activity. Most drugs act by interacting with a protein. Drugs that increase rates or stimulate activities of a protein are called herein "activating drugs," while drugs that decrease rates or inhibit activities of a protein are called herein "inhibiting drugs."

In addition to drugs, this invention is equally applicable to those changes in or aspects of the physical environment that perturb a biological system in targeted manners. Such environmental changes can include moderate changes of temperature (e.g., a temperature elevation of 10° C.) or exposure to moderate doses of radiation. Other environmental aspects include the nutritional environment, such as the presence of only particular sugars, amino acids, and so forth.

The biological effects of a drug (or a physical environmental change) are detected in the instant invention by measurements and/or observations made on the biological state of a cell. The biological state of a cell, as used herein, is taken to mean the state of a collection of cellular constituents, which are sufficient to characterize the cell for an intended purpose, such as for characterizing the effects of a drug. The measurements and/or observations made on the state of these constituents can be of their abundances (i.e., amounts or concentrations in a cell), or their activities, or their states of modification (e.g., phosphorylation), or other measurement relevant to the characterization of drug action. In various embodiments, this invention includes making such measurements and/or observations on different collections of cellular constituents. These different collections of cellular constituents are also called herein aspects of the biological state of the cell. (As used herein, the term "cellular constituents" is not intended to refer to known subcellular organelles, such as mitochondria, lysozomes, etc.)

One aspect of the biological state of a cell usefully measured in the present invention is its transcriptional state. The transcriptional state of a cell is the identities and abundances of the constituent RNA species, especially mRNAs, in the cell under a given set of conditions. Preferably, a substantial fraction of all constituent RNA species in the cell are measured, but at least, a sufficient fraction is measured to characterize the action of a drug of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell is defined herein to be the identities and abundances of the constituent protein species in the cell under a given set of conditions. Preferably, a substantial fraction of all constituent protein species in the cell are measured, but at least, a sufficient fraction is measured to characterize the action of a drug of interest. The transcriptional state of a cell can often be used as a representative of the translational state of a cell.

Other aspects of the biological state of a cell are also of use in this invention. For example, the activity state of a cell, as that term is used herein, refers to the activities of the constituent protein species (and also optionally catalytically active nucleic acid species) in the cell under a given set of conditions. The translational state of a cell can often be used as a representative of the activity state of a cell. This invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

As a result of regulatory, homeostatic, and compensatory networks and systems known to be present in cells, even an "ideal drug," i.e., a drug that directly affects only a single constituent in a cell, and without direct effects on any other constituent, will have complicated and often unpredictable indirect effects. Accordingly, drug administration will typically affect many constituents of whatever aspect of the biological state of a cell is being measured and/or observed in a particular embodiment of this invention. For example, a drug directly affecting only one protein usually causes changes in the expression of many genes. The direct target of even an ideal drug cannot, therefore, be discerned simply by examining the observed changes in the measured aspect of the biological state. Accordingly, this invention provides methods by which controlled observations and/or measurements of the biological state can be interpreted to yield the direct targets of a drug (or of a physical environmental change).

Consider, for example, a drug that specifically and completely inhibits activity of a single hypothetical protein, protein P. Although the drug itself will directly change the activity of only protein P, additional cellular constituents that are inhibited or stimulated by protein P, or which are elevated or diminished to compensate for the loss of protein P activity will also be affected. Still other cellular constituents will be affected by changes in the levels or activity of the second tier constituents, and so on. Therefore, the direct effect of the drug on its target, protein P, is hidden in the large number of indirect effects downstream from protein P.

A drug that is not ideal, e.g., one that directly affects more than one molecular target, may have still more complicated downstream effects. In one aspect, according to the present invention, the analysis of these changes provides considerable information about the drug, including, for example, identification of the direct target or targets of the drug. In a related aspect, the present invention provides methods for carrying out this analysis.

Measurement of the transcriptional state of a cell is preferred in this invention, not only because it is relatively easy to measure but also because, although a drug may act through a post-transcriptional mechanism (such as inhibition of the activity of a protein or change in its rate of degradation), the administration of a drug to a cell almost always results in a change, through direct or indirect effects, in the transcriptional state. A reason that drug exposure changes the transcriptional state of a cell is because the previously mentioned feedback systems, or networks, which react in a compensatory manner to infections, genetic modifications, environmental changes, including drug administration, and so forth, do so primarily by altering patterns of gene expression or transcription. As a result of internal compensations, many perturbations to a biological system have only a muted effect on the external behavior of the system. Nevertheless, the internal response of individual elements, e.g., gene expression, in the cell may be profound. For example, it is estimated that no more than about one-fifth of the genes of the eukaryote, *Saccharomyces cerevisiae*, are essential for cell growth (Nasmyth, 1996, At the heart of the budding yeast cycle, TIG 12:405–412). Genes in the remaining four fifths can usually be individually deleted without preventing cell growth.

Certain terms advantageously used herein to describe drug activity are described below. As used herein, the "target" or "targets" of a drug are the cellular constituent(s), such as gene(s) or gene products including RNAS, proteins, protein activities, and so forth, that are "directly" "affected" by the drug. As used herein, a drug "affects" a cellular constituent (such as a gene, or a gene product, or a gene product activity) in a cell when administration of the drug detectably changes the abundance, or biological activity, or some other measurable property of that cellular constituent. A cellular constituent (such as a gene, a gene product, or a gene product activity) is "directly" affected by a drug when the effect does not require the intervening action of a different cellular constituent (such as a different gene or a product of a different gene). In contrast to a direct effect, a second cellular constituent may be indirectly affected by a drug, for example, when the drug directly changes the abundance or activity of a first cellular component, and this change in turn results in a detectable change in abundance or activity of the second cellular constituent (e.g., a mRNA, a protein, or a protein activity).

For example, FK506, an immunosuppressive drug, can directly affect the activity of a FK506 Binding Protein (FKBP) by binding to such a protein. This change in a FKBP activity can then indirectly (through the action of calcineurin) affect the transcript level of glucon synthase. Here, FKBP is a direct target of the drug FK506, while the glucon synthase protein is an indirect target, requiring the intervening action of other proteins.

Genes and gene products required for the overall health and vitality of the cell are not considered herein to exert such an intervening action. It will be recognized by those of skill in the art that, although certain genes and gene products are required for vitality of the cell, e.g., genes encoding certain metabolic enzymes, ribosomal proteins, etc., and are thus necessary for drug action, this necessity does not, in the context of drug action, constitute an intervening action by these general metabolic genes and gene products.

The term "target" has several specializations and aspects of use in describing the present invention. First, in many cases, a drug will have one cellular direct target, through which it exerts its desired therapeutic effects, along with other cellular direct targets, from which side-effects are derived. In this case, herein, the therapeutic target can be called the "primary (direct) target", and the side-effect targets called the "secondary (direct) targets."

Further, the terms "target", "molecular target" and "genetic target" are used herein interchangeably. In the case in which a drug changes the activity of a protein, the gene encoding the affected protein is also referred to herein as a "target" of the drug, notwithstanding the fact that the abundance of products of that gene (including RNAs and proteins) may or not change in response to the drug. Although most drugs now known, in fact, act by changing an activity or state of a protein, often by some physical interaction with the target protein, as used herein, the protein activity, or the protein abundance, or the RNA encoding the protein, or the gene encoding the RNA are all referred to as the direct "target" of a drug, without regard to which (if any) of these molecules is physically contacted by the drug. The physical interaction of a drug with a protein can occur by several mechanisms, including, direct binding, or interfering with the binding of another molecule to the protein, or other mechanisms.

Further, as is known to those of skill in the art, drugs (e.g., the drug FK506) occasionally act by binding to a receptor protein, which drug-receptor protein complex then directly alters DNA transcription from one or more genes. Although it is strictly true that the only properly named direct target here is the receptor protein (or the receptor protein gene, or the receptor protein activity), in such case where it is the drug-receptor complex that is active, as used herein in this case, the directly targeted gene whose transcription is affected is also referred to as a target (or an "apparent direct target") according to the present invention.

Overview of the Method of this Invention

The present invention provides new and powerful methods for identifying the cellular constituent(s) (e.g., a gene, or a gene product, or a gene product activity) that is the molecular target(s) of a drug or drug candidate. Moreover, the invention provides, inter alia, methods for identifying the cellular consequences of drug treatment, for ranking drugs with similar modes of action for potency and specificity, for identifying primary and secondary targets (e.g., cellular constituents such as genes or gene products) that can produce desired therapeutic outcomes if inhibited or activated, and for producing a "fingerprint" capable of identifying drugs with toxic side effects.

The invention is related, in part, to the discovery that, by examining the effects of a drug in a wild-type cell and comparing those effects with the effect of modifying one or more (usually one) cellular constituents (e.g., deleting a gene), the identity of the direct drug target(s) can be narrowed from the set of all cellular constituents perturbed by the drug to a relatively small set of actual direct drug targets. The invention is also related, in part, to the discovery that by examining the effects of the drug in one or more cells that contain a modification (e.g., modification of a protein activity) at a locus of a potential drug target, the identity and/or nature of the drug target or targets can be determined.

Accordingly, this method involves observing changes in one or more aspects of the biological state of a cell (e.g., changes of the transcriptional state, the translational state, the activity state, or other aspects of the biological state) when subject to various related conditions, and then comparing the observed changes. These observations of changes in aspect(s) of the biological state are preferably made on a cell subject to some or all of the following conditions: exposure of a wild-type cell to a drug, modification of a known cellular constituent of a wild-type cell (thereby creating a "modified cell"), and exposure of modified cells to the drug. The direct targets in the cell of the drug can then be identified by comparing these observed changes and by analyzing these comparisons according to further methods of this invention.

Modifications to a cellular constituent, which can be advantageously employed in the instant invention, are those which precisely target a cellular constituent (e.g., one gene, gene product, one gene product activity, or so forth) in the cell and change it, either by increasing or decreasing, its abundance or activity. Exemplary of such modifications are those that change mRNA abundances, protein abundances, or protein activities. For example, an mRNA abundance, and thus the abundance of the resulting protein as well as its net activity in the cell, can be decreased by deleting or otherwise mutating the encoding gene to no longer produce any mRNA or to produce an mRNA which is translated into a non-functional protein. An mRNA abundance can be increased by introducing a plasmid that constitutively expresses that mRNA, or by altering the promoter or enhancer elements of the gene encoding the RNA to increase its transcription, or by other means. Protein abundances can be directly decreased by increasing their degradation, such as by increasing their ubiquitination. Protein activities can be altered, either increasing or decreasing, by exposure to non-native drugs or native ligands that interact exclusively with the target protein or by dominant negative mutations.

In the case of an embodiment in which genetic components are modified, the effects of increasing or inhibiting expression of individual genes in the cell can be conveniently and exhaustively examined by using a library of cell mutants in which each mutant has been modified at a different genetic locus, such as by gene deletion (to decrease the associated gene product) or non-native promoter insertion (to increase the associated gene product). Such a library is herein called a "compendium" of mutant (or modified) cells. In the general case, a compendium can also be constructed from cells modified at cellular constituents, for example proteins, defining a particular aspect of the biological state.

A simple initial example of the methods of this invention is the case of their application to identifying the direct target of an inhibiting drug by observing the transcriptional state of the cell and by using modified cells constructed by single gene deletions. Where the inhibiting drug has a single direct target, it will be readily appreciated that this target can be simply identified as the gene whose deletion eliminates all the measured transcriptional effects of the drug. Clearly, if the single direct target of the drug is deleted in a modified cell, then the drug can have no effects in that modified cell. All the drug effects are said to "drop out." Accordingly, the transcriptional state of the modified cell will be observed to be substantially unchanged by exposure to the drug. In general, one of several direct targets can be identified as a gene whose deletion eliminates just those transcriptional effects of the drug that are the same as the transcriptional effects due to deletion of the gene alone. Clearly, if a particular gene is a direct target of an inhibiting drug, then the effects of the drug eliminated by deletion of the particular gene, i.e., its effects due to interaction with that particular gene, will be substantially the same as the effects of the deletion of the gene itself. The effects of gene deletion can be directly observed. The effects of the drug due to interaction with the particular gene can be observed by exposing to the drug a modified cell with that gene deleted, whereby such effects will be apparent as those drug effects eliminated (or which "drop out") due to the deletion of the particular gene. By comparing these two observations, it can be determined if the particular gene is a direct target of the drug.

Accordingly, in somewhat more detail in this case, the general methods of this invention make a first observation of the changes in the transcriptional state (defined by RNA abundances) of a wild-type cell due to drug exposure. Next, the method makes a plurality of second observations, each second observation recording the changes in the transcriptional state caused by the deletion of one gene from the wild-type cell. Preferably, the plurality of genes individually deleted are those potentially involved in the action of the drug. The method then makes a further plurality of third observations, each third observation recording changes in the transcriptional state due to drug exposure in a wild-type cell having one of the plurality of genes deleted. The transcriptional effect of the drug that is eliminated from cells in which a particular gene is deleted can be found by comparing the third observations with the first observation. The results of this comparison are then compared with the second observations, which record the transcriptional effects due to deletion of that particular gene alone. If for a particular gene, the transcriptional effects of deleting that gene are the same as the transcriptional effects of the drug eliminated by deleting that gene, then that particular gene is a direct target of the drug.

5.2 Methods for Drug Target Screening

This section presents first the general methods of this invention, presents second certain alternative embodiments of this invention, and presents third applications of the methods of this invention to drug design.

The General Methods of this Invention

The methods of this invention employ certain types of cells, certain observations of changes in aspects of the biological state of a cell, and certain comparisons of these observed changes. In the following, these cell types, observations, and comparisons are described in turn in detail.

The present invention makes use of three principal types of cells: wild-type cells, modified cells, drug-exposed cells. "Wild-type" cells are reference, or standard, cells used in a particular application or embodiment of the methods of this invention. Being only a reference cell, a wild-type cell, need not be a cell normally found in nature, and often will be a recombinant or genetically altered cell line. Usually the cells are cultured in vitro as a cell line or strain. Other cell types used in the particular application of the present invention are preferably derived from the wild-type cells. Less preferably, other cell types are derived from cells substantially isogeneic with wild-type cells. For example, wild-type cells might be a particular cell line of the yeast *Saccharomyces cerevisiae*, or a particular mammalian cell line (e.g., HeLa cells). Although, for simplicity this disclosure often makes reference to single cells (e.g., "RNA is isolated from a cell deleted for a single gene"), it will be understood by those of skill in the art that more often any particular step of the invention will be carried out using a plurality of genetically identical cells, e.g., from a cultured cell line.

Two cells are said to be "substantially isogeneic" where their expressed genomes differ by a known amount that is preferably at less than 10% of genetic loci, more preferably at less that 1%, or even more preferably at less than 0.1%. Alternately, two cells can be considered substantially isogeneic when the portions of their genomes relevant to the effects of a drug of interest differ by the preceding amounts. It is further preferable that the differing loci be individually known.

"Drug-exposed" cells are, briefly, either wild-type cells or modified cells that have been exposed to a drug of interest.

"Modified cells" are derived from wild-type cells by modifications to a particular cellular constituent. Methods of modification are adaptable to this invention if they alter, either by increasing or decreasing, preferably only a single targeted cellular constituent, or less preferably at most only a few targeted cellular constituents (e.g., from 2 to 5 cellular constituents), that influence the aspect of the biological state of a cell measured in an embodiment of this invention. Preferable modification methods are capable of individually targeting and altering many measured cellular constituents relevant to an aspect of the biological state, and most preferably are capable of targeting and altering a substantial fraction of such cellular constituents. For example, preferable modification methods are capable of targeting and altering, e.g., a substantial fraction of all the genes, proteins, or protein activities in a cell, or at least a substantial fraction of those constituents relevant to characterizing the effects of a drug of interest. Where the alteration due to a modification results in the decrease of a cellular constituent, the modification can be referred to herein as a "disruption" of that cellular constituent.

As is commonly appreciated, protein activities result from protein abundances; protein abundances result from translation of mRNA (balanced against protein degradation); and mRNA abundances result from transcription of DNA (balanced against mRNA degradation). Therefore, genetic level modifications to a cellular DNA constituent alters transcribed mRNA abundances, translated protein abundances, and ultimately protein activities. RNA level modifications similarly alter RNA abundance and protein abundances and activities. Protein level modifications alter protein abundances and activities. Finally, protein activity modifications are the most targeted modification methods. As is commonly appreciated, it is ultimately protein activities (and the activities of catalytically active RNAS) that cause cellular transformations and effects. Also, most drugs act by altering protein activities.

Of the many modification methods available for application to the instant invention, those most appropriate to an embodiment in which a specific aspect of the biological state of cells is measured modify the cellular constituents measurable in that aspect. For example, modification methods most appropriate to embodiments measuring the transcriptional state can alter the expression of one gene (e.g., by causing its substantial deletion); methods most appropriate to measurements of the translational state can alter the abundance of one protein (e.g., by causing its substantial ubiquitination); and methods most appropriate to measurement of the activity state can alter the activity of one protein (e.g., by causing substantial binding to its active site).

Certain care must be taken in embodiments in which an aspect of the biological state of a cell is measured that is of a type or level not directly modified by the modification methods used or directly affected by a drug of interest. For example, the effects of modification on a particular cellular constituent that is considered herein as a target of a drug may not be directly measured if the modification is made at a level which does not affect the measured level. For example, in an embodiment measuring transcriptional state, direct modifications to the activity or abundance of a particular protein will not be reflected in the transcriptional state of the mRNA encoding that modified protein, although all the secondary transcriptional effects of modifying the protein abundance of activity will be measured. For a further example, the effects of modifying a direct drug target may differ from the effects of the drug on the target itself. In an embodiment measuring the transcriptional state, if a drug of interest directly modifies the activity of a protein (as is typical), genetic modifications of the DNA encoding this protein will mimic the drug effects except in that the level of the mRNA and the protein abundances of the target will also be changed. Therefore, in comparing perturbation patterns (see below) in such cases it may be necessary to ignore perturbations at a putative direct target.

In the case of genetic level modification methods, two types of modified wild-type cells of particular interest are deletion mutants and over-expression mutants. Deletion mutants are wild-type cells that have been modified genetically so that a single gene, usually a protein-coding gene, is substantially deleted. As used herein, deletion mutants also include mutants in which a gene has been disrupted so that usually no detectable mRNA or bioactive protein is expressed from the gene, even though some portion of the genetic material may be present. In addition, in some embodiments, mutants with a deletion or mutation that removes or inactivates one activity of a protein (often corresponding to a protein domain) that has two or more activities, are used and are encompassed in the term "deletion mutants." Over-expression mutants are wild-type cells that are modified genetically so that at least one gene, most often only one, in the modified cell is expressed at a higher level as compared to a cell in which the gene is not modified (i.e., a wild-type cell). Alternatively and less preferably, the deletion and over-expression mutants may not be derived from the wild-type cells but may instead be derived from cells that are substantially isogeneic with wild-type cells, except for their particular genetic modifications.

Among RNA level modification methods are those employing antisense constructs and ribozymes. Antisense constructs act by hybridizing to a target mRNA (or DNA) and hinder or prevent its translation (or transcription) into the target protein. A cell may be exposed to antisense constructs, or antisense nucleic acids may be expressed in the cell. Ribozymes are catalytically active small RNA sequences that target and cleave specific RNA sequences. They can be expressed in a cell in order to decrease or eliminate a targeted mRNA, and consequently to decrease a targeted protein abundance.

Abundance of targeted proteins can be decreased by numerous methods. For example, the rate of ubiquitination of a targeted protein can be increased in order to increase its rate of degradation. Antibodies to a targeted protein can be introduced into a cell or expressed intracellularly in order to bind the protein intracellularly into non-wild-type, possibly multimeric, structures that are substantially less active than the wild-type structures A protein activity can be directly targeted and modified by, e.g., exposure of a cell to drugs with well-characterized direct targets. Preferably, drugs so employed are "ideal", each having only a single direct target in the cell. Less preferably, the drugs employed each have only a few direct targets, each target of a drug having independent and non-overlapping effects on aspects of the biological state of the cell. Drugs can be employed to either inhibit or stimulate a targeted protein activity. They can be, for example, standard small molecular drugs, neutralizing or activating antibodies, or natural ligands for receptors that inhibit or activate a targeted activity of interest. In another method of modifying protein activity, mutant alleles can be expressed in the cell which inhibit the activity in a dominant manner ("dominant negative mutations"). Such dominant negative mutants can act, inter alia, by flooding the cell with an inactive form of the protein which nevertheless binds the natural substrate, or by introducing mutant subunits which render a multimeric structure inactive, or by other known means. For example, a mutant subunit with an activity domain deleted but retaining an association domain (as can be formed by partial gene deletions) can form inactive multimeric complexes. Other well-known methods of protein inactivation can also be used, for example, temperature sensitive mutant forms.

This invention is adaptable to the other forms of cellular modification methods that can be targeted to specific cellular constituent.

The method of the invention involves observing changes in any of several aspects of the biological state of a cell (e.g., changes in the transcriptional state, in the translational state, in the activity state, and so forth) between a wild-type cell in different states or with different modifications, or exposed to a drug. A relative increase or decrease in response to, e.g., exposure to a drug or to a genome modification, in the abundance or activity of a cellular constituent measured in an aspect of the biological state of the cell (e.g., specific mRNA abundances, protein abundances, protein activities, and so forth) is called a perturbation. An increase is called a positive perturbation, and a decrease a negative perturbation. No significant detectable change is called no perturbation. The set of perturbations observed for cellular constituents (including, optionally, cellular constituents with no perturbation) can be referred to as a perturbation pattern or a perturbation array. Depending on the measurement techniques, perturbations may be scored qualitatively simply as a positive, a negative, or no perturbation, or actual quantitative values may be available and compared. For example, a perturbation pattern or array can be a pattern of changes in mRNA abundances, protein abundances, protein activity levels, or so forth.

As used herein, perturbations of a first and a second cellular constituent (that are the same or different and are from the same or a different cell) that are being compared are said to be "differently perturbed" when for the first cellular constituent there is a positive perturbation, or no perturbation, or a negative perturbation, and for the second cellular constituent there is no perturbation or a negative perturbation, or a positive or a negative perturbation, or no perturbation of a positive perturbation, respectively. In cases where the values of perturbations are measured, two perturbation can be said to be "differently perturbed" where the measured values for the two perturbations are detectably different, preferably having a statistically significant difference. As used herein, perturbations of a first and a second cellular constituent are said to be the "same" when both have a negative or a positive perturbation, or where the measured values are not significantly different.

The actual values present in a perturbation pattern depend essentially on the measurement methods available for the particular cellular constituents being measured. Where quantitative abundances or activities are available, either in absolute or relative units, a numerical abundance or activity ratio can be calculated and placed in the perturbation pattern. For example, in the case of transcriptional state measurements by quantitative gene expression technologies, a numerical expression ratio of the abundances of cDNAs (or mRNAs in an appropriate technology) in the two states can be calculated. Alternatively, a logarithm (e.g., $\log_{10}$) (or another monotonic function) of the abundance ratio can be used. Where only qualitative data is available, arbitrary integer values can be assigned to each type of perturbation of a cellular constituent. For example, the value +1 can be assigned to a positive perturbation; the value −1 to a negative perturbation; and the value 0 to no perturbation.

It is often convenient to represent graphically a perturbation pattern or array as a two-dimensional physical array of perturbation values. When making such a graphical representation, the assignment of particular perturbation values to particular array positions can be entirely arbitrary or can be guided by any convenient principles. For example, related cellular constituents, such as genes, proteins, or protein activities of a particular pathway, can be grouped together. In the case of transcriptional state measurements by gene transcript arrays, the perturbation pattern or array can be arranged as the transcript array is arranged.

In preferred embodiments, the effects of a drug are determined by observing and comparing changes in the transcriptional state of a cell. Although homeostatic mechanisms in cells are not limited to transcriptional controls, analysis of the transcriptional state is often found sufficient for purposes of drug characterization and drug discovery. First, most drugs produce a significant and characteristic change in the transcriptional state of the cell. For example, the inventors have discovered that nearly every drug-effect observed in yeast results in changes to specific transcript levels. Second, because homeostatic control mechanisms acting at a variety of levels in cells generally appear to move in the same direction, corresponding cellular constituents at the transcriptional level, the translational level, and the activity level often change in the same direction. For example, the down regulation of cyclin transcription in yeast is accompanied by cyclin inactivation by phosphorylation and degradation by ubiquitin-mediated proteolysis (Nasmyth, 1996, At the heart of the budding yeast cycle, TIG 12:405–412). Thus, a cellular response that activates (or inhibits) the activity or prevalence of a given protein at one level is often accompanied by a corresponding transcript induction response.

The methods of the present invention identify drug targets by observing and comparing perturbation patterns recording differences between wild-type cells in particular states or conditions. The perturbation patterns preferably observed are: (1) the wild-type drug perturbation pattern, (2) the modified-cell perturbation pattern, and (3) the modified-cell drug perturbation pattern. These patterns are described in detail in the following.

The wild-type cell drug perturbation pattern includes perturbation values that represent the perturbation in cellular constituents observed in an aspect of the biological state of a wild-type cell resulting from exposure to a drug of interest. An aspect of the biological state of a wild-type cell exposed to a drug is measured and compared to that aspect of the biological state of the cell not exposed to a drug in order to determine the cellular constituents in this aspect that are perturbed or are not perturbed. This type of perturbation pattern provides information about the effect of the drug on the biological state of the cell (e.g., on the transcriptional or translational state of the cell), specifically the characteristic manner in which the biological state of the cell changes when the cell is exposed to the drug. This perturbation pattern includes changes due not only to the effect of the drug on its direct targets in the cells but also the typically numerous indirect effects of the drug, which are mediated by the homeostatic feedback systems and networks previously mentioned.

The modified-cell perturbation pattern includes perturbation values that represent the perturbation in cellular constituents observed in an aspect of the biological state of a wild-type cell resulting from an indicated cellular modification by, e.g., gene deletion, protein inhibition, or so forth. An aspect of the biological state of a wild-type cell with a modification to a cellular constituent is measured and compared to that aspect of the biological state of the cell without such a modification in order to determine the cellular constituents in this aspect that are perturbed or are not perturbed. Such a perturbation pattern is not generally limited to revealing only changes directly due to the modification, because changes in the elements of the biological state that are indirectly affected by the particular modification or its products will also be apparent (as is the case also for the wild-type drug perturbation pattern). This type of perturbation pattern provides information about the effects of the cellular constituent modified on the biological state of a wild-type cell. The methods of this invention compares these effects with drug effects to identify drug targets. A group of these perturbation patterns (called herein a compendium of perturbation patterns) is optionally but conveniently assembled for systematic screening for drug targets.

It will be recognized by those of skill in the art that the modified-cell perturbation pattern for modification to a particular cellular constituent will be the same (except perhaps for the cellular component which is directly modified, see above) as a wild-type drug perturbation pattern for an "ideal" drug that has precisely this cellular constituent as its direct target. In the case of a gene deletion modification, it will be apparent that perturbation pattern includes the absence of transcripts from the deleted gene. A drug that completely inhibits the translated protein will have the same effect as such a deletion of the gene for that protein with the exception that the translated target protein will still be present in the cell (though inactive).

The modified-cell drug perturbation pattern includes perturbation values that represent the perturbation in cellular constituents observed in an aspect of the biological state of a wild-type cell with a modification to a specific cellular constituent (e.g., gene deletion, protein inhibition, or so forth) resulting from exposure to a drug. An aspect of the biological state of a wild-type cell with a modification to a specific cellular constituent and exposed to the drug is measured and compared to that aspect of the biological state of the cell with the modification but not exposed to the drug in order to determine the cellular constituents in this aspect that are perturbed or are not perturbed. This pattern provides information on the interaction of the drug with the cellular constituent modified by revealing those effects of the drug on the biological state of a wild-type cell that survive or do not survive in the presence of the indicated modification. By comparing, as subsequently described, modified-cell drug perturbation patterns with both modified-cell perturbation patterns and wild-type cell drug perturbation patterns according to the methods of this invention, an investigator can determine the direct targets of the drug.

In a specific embodiment, in which the modifications to wild-type cells are genetic modifications, in which the observed aspect of the biological state is the transcriptional state, and in which the transcriptional state is measured by hybridization to a gene transcript array, these perturbation patterns or arrays are measured in the following ways. The wild-type drug perturbation pattern is determined by observing the wild-type drug transcript array; the modified-cell perturbation pattern is determined by observing the mutant transcript array; the modified-cell drug perturbation pattern is determined by observing the mutant drug transcript array. In particular, deletion transcript arrays, where the genome modification includes gene deletion, and over-expression transcript arrays, where the genome modification includes gene over-expression, are examples of mutant transcript arrays. These perturbation patterns or arrays preferably have the same physical layout as the layout of the nucleic acids on the surface of this transcript array. Even where the transcriptional state is measured by other gene expression technologies, it can be convenient to refer to these perturbation patterns as "transcript arrays."

In view of the previously described cell types, perturbations, and perturbation patterns, the methods for drug characterization according to the present invention identify direct drug targets by observing and comparing perturbation pattern. In one preferred general embodiment, these methods includes a series of four principal steps. The first step includes observing the wild-type drug perturbation pattern, in which patterns are identified of cellular constituents of the measured aspect of the biological state that are perturbed when a wild-type cell is exposed to the drug. When the transcriptional state is observed, the cellular constituents are mRNA species and perturbations are represented by relative increases or decreases in abundances of mRNA species (e.g., compared to a cell that is not exposed to the drug). Alternatively, when the translational state is observed, the cellular constituents are protein species, and the perturbation may be a change in the abundances or activities of protein species.

The second step includes identifying cellular constituents whose modification in a wild-type cell results in perturbation of at least one cellular constituent that is also identified as perturbed in the wild-type drug perturbation pattern observed in the first step. This step can be performed by observing a plurality of modified-cell perturbation patterns generated by modification of a plurality of cellular constituents (i.e., a compendium), and selecting those cellular constituents whose modified-cell perturbation patterns share at least one perturbed cellular constituent in common with the wild-type drug perturbation pattern. Preferably, the plurality of cellular constituents modified include those which are likely to be relevant to the action of the drug. In this manner, cellular constituents are found each of whose modification have, at least at one cellular constituent minimally, similar effects on the biological state of a cell as exposure to the drug, in that both the modification of one of these cellular constituents and the exposure to the drug perturb at least that one cellular constituent similarly. These cellular constituents are thereby identified as potential drug targets. This step can be performed either by initially identifying a plurality of such cellular constituents sharing an effect with the drug, or alternatively, by identifying one such cellular constituent and then proceeding with the remaining steps of this methods before identifying the next such cellular constituent.

For example, in cases where the modifications are gene deletions and the observations are of the transcriptional state of a cell, this step can be performed by observation of the modified-cell transcriptional perturbation patterns resulting from deletion of genes that may be relevant to the action of the drug, followed by comparison with the wild-type drug transcriptional perturbation pattern. Alternatively, where the modifications are gene deletions and the observations are of the translational state of a cell, this step can be performed by observation of the modified-cell translational perturbation pattern (i.e., abundances or activities of proteins in the cell, the "proteome") resulting from the deletion of genes that may be relevant to the action of the drug, followed by comparison with the wild-type drug translational perturbation pattern.

In one alternative, the cellular constituents sharing an effect with the drug can be ranked, with those cellular constituents sharing more effects with the drug being ranked ahead of those cellular constituents sharing fewer effects with the drug. It is advantageous to perform the further steps of the methods of this invention first, for more highly ranked cellular constituents, since the more highly ranked cellular constituents are more likely to be drug targets. Cellular constituents can also be ranked according to the correlation coefficient of their modified-cell perturbation pattern with the wild-type drug perturbation pattern.

The third step includes observing modified-cell drug perturbation patterns for those cellular constituents identified in the second step whose modification in a wild-type cell results in at least a minimum of effects on the cell that overlap with the effects of exposure of the wild-type cell to the drug.

The fourth step compares the previously observed wild-type drug perturbation pattern, the modified-cell perturbation patterns, and the modified-cell drug perturbation patterns to identify cellular constituents that are direct targets of the drug. The following comparisons are made for each cellular component modified. First, the modified-cell drug perturbation pattern is compared to the wild-type drug perturbation pattern in order to identify the "drop-out" pattern of cellular constituents for the particular cellular constituent modified. Cellular constituents "drop out" when they are perturbed in the wild-type drug perturbation pattern (i.e., perturbed in a drug-exposed wild-type cell), but are not similarly perturbed or are not perturbed at all in the modified-cell drug perturbation pattern (i.e., differently perturbed in a drug-exposed modified cell). In other words, a target cellular constituent "drops out" if the modification to the particular cellular constituent eliminates (or changes) the effect of the drug on the target cellular constituent. By comparing the behavior of cellular constituents present in these two perturbation patterns, cellular constituents that "drop out" due to the modification of the particular cellular constituent can be determined. All cellular constituents identified to drop out are collectively referred to herein as the "drop-out set."

Second, the "drop-out" pattern (or, equivalently, the drop-out set) determined for the modification of a particular cellular constituent (i.e., those cellular constituents whose drug effects are eliminated or changed by modification alone of the particular cellular constituent) is compared to the modified-cell perturbation pattern generated by modification of that particular constituent (i.e., the cellular constituents perturbed by the modification of the particular cellular constituent without drug exposure). If these two patterns are the same, then that particular cellular constituent is identified according to this invention as a direct target of the drug.

Certain optional steps can supplement the four principal steps. In a first option, after the second step, the modified-cell perturbation patterns can be immediately compared to the wild-type drug perturbation pattern. If one of the modified-cell perturbation patterns is found to be identical or substantially identical to the wild-type drug perturbation pattern, this one cellular constituent can be immediately identified as the single, direct target of the drug. In making this comparison, the perturbation of this one particular cellular component may need to be ignored. For example, if a drug completely inhibits protein P, which is encoded by gene G, then deletion of gene G will have the same effects as the drug in addition to the effect of eliminating protein P itself from the cell. (In this case, according to the usage herein, both protein P and gene G are considered to be direct targets of the drug.)

A second optional step identifies all the cellular constituents available for modification that are direct drug targets. Substantially all the direct targets can be identified if substantially all the cellular constituents measured in an aspect of the biological state of a cell can be modified or at least those cellular constituents relevant to action of the drug. This step causes repetition of the comparisons made in the fourth step until all the cellular constituents available for modification have been tested by the steps of this embodiment. If as a result all the cellular constituents perturbed in the wild-type drug perturbation pattern have been identified as drop-outs eliminated from the drug effect in some modified cell, then the identified direct targets are all the direct targets of the drug.

5.2.1 Alternative Embodiments

This subsection describes alternative embodiments relating to construction of modified-cell perturbation patterns, namely "compendiums" of modified-cell perturbation patterns, to comparisons of perturbation patterns, namely use of correlation coefficients and other statistical tools, and to further examples of the methods of this invention.

In one alternative embodiment, a compendium, or database, of modified-cell perturbation patterns is first observed and then subsequently utilized to identify the direct targets of one or more drugs. The compendium, or database, is constructed by observing modified-cell perturbation patterns for modifications to a large plurality of cellular constituents. This large plurality preferably includes all cellular constituents that may be involved in the action of one of more drugs of interest, or more preferably includes a substantial fraction of all the cellular constituents of that type in that aspect of the biological state of the cell. For example, when the modifications are made by gene deletions in a wild-type cell whose genome is substantially known (e.g., the yeast *Saccharomyces cerevisiae*), methods known in the art may be used to systematically create deletion mutants (or gene knockouts) for a substantial fraction of the genes in the genome (see below).

Accordingly, in a particular alternative embodiment in which modifications are made by gene deletions and in which the transcriptional state of cells is observed, the present invention provides the following steps for determining the effect of a drug on a cell by: (1) constructing a compendium of deletion transcript arrays, in which each deletion transcript array depicts the transcriptional state in a cell in which a single gene has been disrupted, (2) preparing a wild-type drug transcript array that depicts the transcriptional state of a wild-type cell exposed to the drug, (3) comparing the wild-type drug transcript array and the deletion transcript arrays of the compendium and identifying the deletion transcript array or arrays in the compendium that correspond to the wild-type drug transcript array. This particular alternative applies equally to over-expression mutants.

Comparison of the transcript array resulting when a cell is exposed to a drug with the transcript array(s) resulting from deletion of a particular gene(s) in a cell will identify the target or potential target(s) of drug action. For example, a drug that specifically and completely inactivates gene expression from only a single gene will produce a drug transcript array that, excepting transcripts corresponding to the deleted gene, is identical or nearly identical (within experimental errors) to the deletion transcript array produced by the cell deleted for that gene. Thus, the molecular target of an "ideal" drug can be determined by comparing the wild-type drug transcript array and the mutant transcript array. (A similar comparison can be made between the wild-type drug transcript array and the over-expression compendium, in which a drug that specifically activates expression of a single gene will produce a drug transcript array that is identical or nearly identical to the over-expression transcript array produced by the over-expression mutant for that gene.)

When a predetermined putative drug target is known, it may not be necessary to construct a compendium of mutant transcript arrays; rather, a single mutant (e.g., deletion) transcript array, corresponding to the putative target, is used. As used herein, a putative drug target is a cellular constituent (e.g., RNA or protein abundances or activities) that is believed to be directly affected by the candidate drug.

In most cases, however, the wild-type drug transcript array will not be identical to a single deletion transcript array. As set forth above, one reason for this is that most drugs affect more than one target. Usually it will be necessary to identify potential targets, and carry out further analysis to verify that the potential targets are actual targets. This further analysis, or "interrogation" involves, in one preferred embodiment, treating cells mutated at the genes encoding the potential targets (e.g. deletion or overexpression mutants) with the subject drug, and comparing the resulting mutant drug transcript arrays to the drug transcript array and to the mutant transcript arrays (e.g., of the compendium) according to the described methods. In particular, if no deletion transcript array corresponds to the wild-type drug transcript array, this further interrogation involves: (4) preparing mutant drug transcript arrays; (5) comparing the mutant drug-transcript arrays to the wild-type drug transcript arrays to find drop-out patterns for particular deleted genes (all the transcripts that drop out can be assembled into a set called, or can be collectively referred to herein as, the "drop-out set"); and (6) comparing the drop-out patterns for particular deleted genes to the mutant transcript arrays for that deleted (or overexpressed) gene to find direct targets of the drug.

It will be immediately appreciated from the foregoing that this particular alternative embodiment can be adapted to other particular alternatives in which different methods of wild-type cell modification are employed and different aspects of the biological state of the wild-type cell are observed.

The methods of this invention call for the comparison of various perturbation patterns or perturbation arrays, such as transcript arrays of various kinds. This comparison of different perturbation patterns or arrays (e.g., a wild-type drug perturbation pattern with a modified-cell drug perturbation pattern) typically involves pair-wise comparisons of the perturbations recorded in each pattern or array for the same cellular constituent. For example, for each cellular constituent whose perturbation is recorded in the arrays, the value of the perturbation recorded in one perturbation pattern may be compared to the corresponding value recorded in the other perturbation pattern to determine whether the same perturbation (e.g., a positive perturbation, negative perturbation, or no perturbation) is found in both patterns or arrays. This comparison may be qualitative or quantitative (i.e., the relative magnitude of the change may be compared), and may be carried out mathematically, graphically, or by any other convenient method.

In one embodiment for comparison of arrays of values, as illustrated in Example 6.5, each pair of values recorded in the two arrays describing the perturbation of one cellular constituent is independently compared and it is determined that the values in the two arrays are the same, or different. The determination that two perturbation values are the same or different is preferably such that this determination is statistically significant according to, e.g., methods set out in the following paragraphs. Where a modified-cell drug perturbation pattern is compared to a wild-type drug perturbation pattern, it is determined that certain sites drop out (all sites that drop-out are collectively known as the "drop-out" set) and other do not (such sites "remain" and are collectively known as the "remaining set").

In a related embodiment for array comparison, the pair-wise comparison is expressed as a correlation coefficient. A correlation coefficient can describe the degree of similarity of two different perturbation patterns or arrays (and thus, e.g., the degree to which the effects on the measured aspect of the biological state of the wild-type cell—such as exposure to a drug and modification of a cellular constituent—are similar or dissimilar). A correlation coefficient for two sets of data (such as two perturbation arrays) may be calculated using statistical methods well known in the art (see, e.g., M. G. Bulmer, *Principles of Statistics*, 1967 Dover Press, New York, e.g., pp. 117 (the log-normal distribution) and pp. 221–224 (correlation coefficients); Tetrault G., 1990, *Clin. Chem.* 36:585; Press et al., *Numerical Recipes in C: The Art of Scientific Computing*, 1993 Cambridge Univ. Press, Cambridge; each of which is incorporated herein by reference in its entirety and for all purposes).

When correlation coefficients are used to describe the relationship of the large number of pairs of corresponding perturbation values in two perturbation arrays, they may be based on any of several types of underlying data. Where measurements of the biological state of a cell yield qualitative, numerical data, as is possible for measurements of the transcriptional state, a ratio of the two values can be calculated (e.g., a ratio of gene expression, protein abundance, protein activity, or so forth), and a correlation coefficient calculated from the calculated ratios of each pair of corresponding perturbation values. Alternatively, a similar correlation coefficient can be calculated where arbitrary integer values are assigned to each type of perturbation (e.g., assigning the value +1 to a positive perturbation; −1 to a negative perturbation; and 0 to no perturbation). The same underlying data can be used for pair-wise comparisons.

In another embodiment, a logarithm (e.g., $\log_{10}$, $\log_2$, $\log_e$, or so forth) of the calculated perturbation value ratio can be used. Computation of the correlation coefficient from logarithms of the perturbation values is advantageous because both induction by a given multiplicative factor and inhibition by that same multiplicative factor result in the same absolute value of the logarithm. Further, the logarithm of perturbation values is often dominated by the (usually) few cellular constituents with the largest perturbation ratios, making it a more robust cell-wide similarity measure. Additionally, when calculating the correlation coefficient, it is often preferable to ignore small changes in perturbation values in order to ignore the experimental biases that can arise between wild-type and modified-cell perturbation patterns. This can be easily accomplished by setting to 0 all perturbation ratios whose absolute value of their base-10 logarithm is less than some threshold. Typical thresholds are preferably less than 0.3, 0.2, 0.1, 0.05, or smaller thresholds, but can be chosen depending directly upon the expected magnitudes or distributions of the experimental biases or variations.

Based on the calculated correlation coefficient for the pair-wise comparisons of perturbations, the degree of similarity of two different perturbation arrays can be determined by standard statistical analysis. A higher value for the correlation coefficient indicates a greater degree of similarity, while a smaller value indicates a lesser degree of similarity. This analysis is used, inter alia, to determine the likelihood that, in a given mutant strain, the mutated gene is a drug target. For example, as illustrated in Example 6.6, a correlation can be computed between the wild-type drug transcript array for the immunosuppressive drug FK506 and the deletion transcript array for a calcineurin mutant (in which coding sequences for both catalytic subunits of calcineurin are disrupted).

Figure 1A:
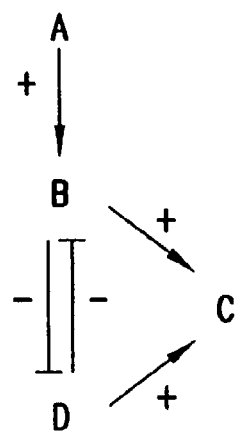
Figure 1B:
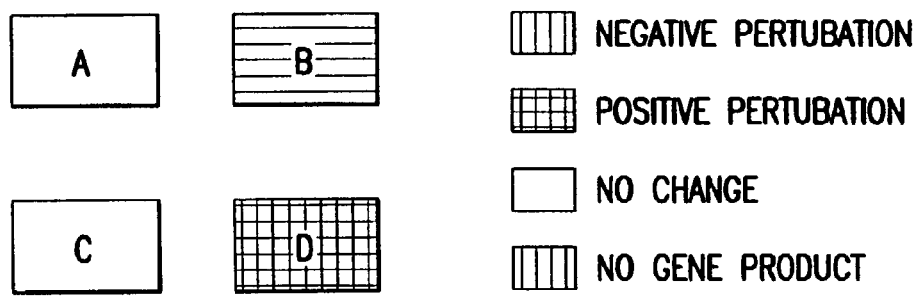
Figure 1C:
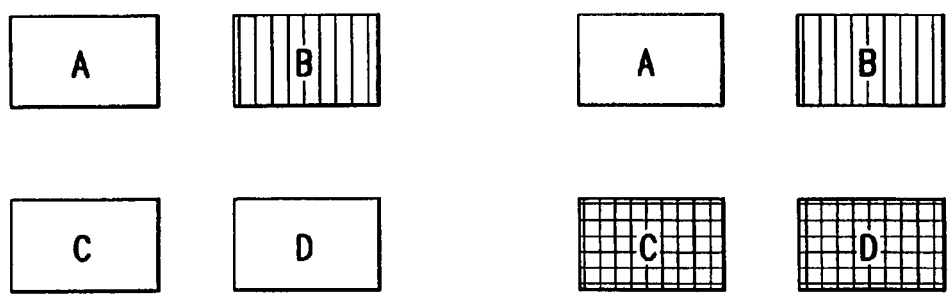

One method of obtaining an estimated error distribution for providing such statistical estimation of the significance of correlation coefficients or the confidence levels ("error bars") of pair-wise comparisons in the case of transcript arrays (see below) is to perform a benchmark experiment. cDNA (or mRNA) is extracted from nominally identical cells, labeled with different fluorescent dyes, and hybridized to a transcript array (i.e., a wild-type vs wild-type transcript array). The distribution of observed expression ratios then indicates the experimental nominal error distribution and can be used to obtain confidence intervals. As will be apparent to one of skill in the art, similar wild-type vs. wild-type benchmark experiments can be used to calibrate measurements of other aspects of the biological state of a cell Examples of Alternative Embodiments The steps of comparing and analyzing observed perturbation patterns have alternatives illustrated in the following examples. A first example is illustrated in FIGS. 1A–1C. In FIG. 1A, a four-element gene network is illustrated, showing the relationship between genes A, B, C, and D. A gene network is used herein to represent the functional links indicating how one gene affects the expression of another gene. In this network, gene A activates gene B, genes B and D each activate gene C, and genes B and D inhibit each other. If a cell is exposed to a drug that completely inhibits transcription from gene B, the resulting wild-type drug perturbation pattern will be similar to that shown in FIG. 1B. However, exactly the same perturbation pattern could result if the cell is exposed to a drug that activates transcription from gene D. As a consequence, if exposure of an uncharacterized drug results in the perturbation pattern shown in FIG. 1B, it would not be possible to determine whether the drug inhibited gene B or activated gene D. This ambiguity is resolved by performing analysis with gene deletion (and/or over-expression) strains. FIG. 1C illustrates that, if the uncharacterized drug is administered to a modified cell that is deleted for gene B, the modified-call drug perturbation pattern resulting from a drug that inhibits gene B can be distinguished from one for a drug that activates gene D. This is because, in a cell deleted for the gene that is, or encodes, a target of the drug, the indirect effects of the drug on other cellular constituents that are "downstream" of the target gene are not reflected in the transcriptional state of the cell. When a drug affects more than one target cellular constituent, a consequence of eliminating the transcriptional changes resulting from the direct and indirect effects of a drug on one target is that the other target(s) can be more easily identified.

A further example of alternative comparison and analysis of perturbation patterns is illustrated by a second example, also related to a drug that directly inhibits activity of a target protein, but does not directly change the level of transcription (or abundance of transcripts) of the target gene (the gene encoding the target protein). Transcription of a gene, designated $B_g$, is controlled by two proteins, $A_p$ and $C_p$. $A_p$ and $C_p$ each induce the transcript, $B_t$, of $B_g$ by a factor of 10 in isolation, and by a factor of 100 in combination. In fact, expression of most genes is believed to be controlled by multiple regulators in this way. If this system is treated with a drug that reduces $B_t$ by 10 fold it will not be possible to determine, on the basis of transcript levels alone in a wild-type cell (e.g., a wild-type drug perturbation pattern), whether the drug acts to inhibit $A_p$ or $C_p$. However, this ambiguity can be resolved by performing experiments with deletion strains. If the drug inhibits $A_p$, then the modified cell deleted for gene A (the gene encoding $A_p$) in combination with the drug will express $B_t$ at 10% of wild type while the modified cell deleted for gene C in combination with drug will express $B_t$ at 1% of wild type. If the inhibitor acts on $C_p$, then the modified cell deleted for gene C will express $B_t$ at 10% of wild type in presence of drug and the modified cell deleted for gene A will express $B_t$ at 1% of wild type in the presence of drug. Thus, the two possibilities in this example can be distinguished in cells modified by gene deletion but not in wild-type cells.

5.2.2 Applications to Drug Discovery

The present invention has numerous applications in the field of drug discovery, some of which are presented herein. In one application, the present invention provides a method in which other targets of a candidate drug for which a putative target has been identified are characterized. As noted supra, drug development often involves testing numerous compounds for a specific effect on a known molecular target, such as a cloned gene sequence or isolated enzyme or protein. In this process, drug candidates that apparently affect the putative target are identified, but little or no information is generated about the specificity of the drug (e.g., what other targets are affected), or about the effects of the drug at the cellular level. The method of the present invention provides this information.

For example, provided with a candidate drug that appears to affect a putative target cellular constituent, the methods of the present invention can be applied to confirm that the putative target is indeed a target of the drug, as well as for development of drugs (e.g., such as an ideal drug) that are more specific for the putative target (i.e., are more target-specific) in that they have fewer targets other than the desired putative target. This application of these methods is outlined generally in FIG. 5. In one aspect, this is accomplished by (i) making a wild-type drug perturbation pattern for the candidate drug; (ii) making a modified-cell perturbation pattern in which the putative target cellular constituent is modified (e.g., if the cellular constituent is a gene, the gene may be deleted); (iii) making a modified-cell drug perturbation pattern, e.g., by using the candidate drug and a modified cell in which the putative cellular component is modified (its abundance or activity is decreased or increased); and (iv) comparing the modified-cell drug perturbation pattern with the wild-type drug perturbation pattern.

If, as is described in more detail supra, the pattern that "drops out" (or the drop out set) upon comparison of the modified-cell drug perturbation pattern and the wild-type drug perturbation pattern matches the perturbation pattern of the modified-cell perturbation pattern this indicates that the putative target is a direct target of the candidate drug. As described supra, cellular components "drop out" when they are perturbed in a wild-type drug perturbation pattern but are differently perturbed in the modified-cell drug perturbation pattern. If the cellular constituents perturbed in the wild-type drug perturbation pattern are substantially the same as the cellular constituents that drop out in the comparison of the modified-cell drug perturbation pattern and the wild-type drug perturbation pattern (in this case at least the same cellular constituents are perturbed in the modified-cell perturbation pattern), then this indicates that the candidate drug is highly specific for the putative target cellular constituent (with few or no direct effects on other cellular constituents, such as genes, or gene products, or gene product activities). If all of the cellular constituents perturbed in the modified-cell perturbation pattern drop out, but other cellular constituents perturbed in the wild-type drug perturbation pattern do not drop out (i.e., remain), then this indicates that the candidate drug targets both the putative target and other cellular constituents.

In the latter case, in which other cellular constituents are targeted, the structure of the candidate drug may be modified (e.g., using organic synthesis methods well known in the arts of pharmaceutical or medicinal chemistry) or closely related compounds may be identified, or the like, and tested according to the present method until a drug that is more target-specific (i.e., having fewer targets other than the putative target) for the putative target (or even an ideal drug having only the putative target as a drug target) is identified.

In another application, the methods can be used to select, from a set of candidate compounds, the drug or drugs with the highest target specificity by identifying all the direct cellular targets of compounds in the set. Usually, the drug with the highest target specificity will be the one that directly affects only its intended target. When the intended target is not known, the drug that affects the fewest number of targets is likely to be more target specific than a drug that affects a greater number of targets and is a preferred candidate. A drug with high specificity (i.e., highly target-specific) is of interest because such a drug will have fewer side effects when administered to a patient.

In further applications, the invention can be used to identify the direct target(s) of a drug that has a known biological effect on cells (or in patients), but for which the mechanism or target is not known. By identifying the direct targets of a drug with a desirable activity it is possible to identify other compounds having a similar activity, as well as to identify compounds with greater target specificity. Conversely, the methods of this invention can be used to identify a compound or compounds that affect a particular pre-determined target in a cell, or that affect a particular combination of targets.

In yet a further application, the method is used to identify "secondary drug loci." Secondary drug loci are cellular constituents of any type (such as genes or gene products or gene product activities), that are indirectly affected by the administration of a drug. They are identified by the fact that they correspond to cellular constituents having positive or negative perturbations in the wild-type drug perturbation pattern, but are excluded as direct targets of the drug. The identification of secondary drug loci is useful in drug design. As discussed above, the homeostatic mechanisms of the cell usually assure that a change in one cellular constituent (e.g., gene, or gene product, or gene product activity) is compensated for by changes in the expression and/or activity of other cellular constituents.

Recognition of these compensatory changes provides a new approach to drug intervention, as follows: Disease can be considered the result of abnormal expression of a cellular constituent (e.g., a gene of a host or a pathogen). Conventional approaches to drug intervention seek to modulate the activity at this primary cellular constituent. However, the present method identifies secondary drug loci, which are cellular constituents, such as genes or gene products, that a drug indirectly affects (e.g., exhibit compensatory changes) when a primary target is directly affected. Using this information, it is possible to identify drugs that affect the secondary cellular constituents, providing alternative approaches to treatment (and a much greater array of potential drug targets). For example, if in a diseased state cellular constituent X is under-expressed, the conventional goal of therapy is to restore the expression of X, and drugs may be identified that achieve this result by directly affecting the expression of X. However, the present method allows identification of other cellular constituents having X as a secondary drug loci, when these other cellular constituents are affected by a drug. Hyper-expression of element X will thereby result. Thus, secondary targets (e.g., proteins, or protein activities) that produce desired therapeutic outcomes if inhibited or activated can be identified, and drugs can be identified that affect these other targets to achieve the desired therapeutic outcome (e.g., restoring the expression of X), other than by direct effects on X.

In additional applications, the methods of this invention can be used to identify cellular constituents that mediate the therapeutic actions or that mediate the side-effects of a drug of interest by comparison of the drug of interest with other drugs having similar therapeutic effects. Two drugs are considered to have similar therapeutic effects if they both exhibit similar therapeutic efficacy for the same disease of disorder. Drugs known to have similar, or closely similar, therapeutic affects are often found to act on the same therapeutic targets. Therefore, the methods of this invention can be applied to determine the targets of the drug of interest and also of a second drug with similar therapeutic effects. Targets that are common to both drugs are those targets likely to mediate the therapeutic effects of the drug of interest (and also of the second drug). By comparing common targets determined for additional drugs with similar therapeutic effects, the targets mediating the therapeutic effects of the drug of interest can be further narrowed or identified.

Similarly, targets of a drug that mediate the side-effects can be determined by the methods of this invention. The targets of the drug of interest and of a second drug with a similar therapeutic effects are determined according to this invention. The targets of the drug of interest that are not also targets of the second drug are likely to be those mediating the side-effects of the drug of interest. By comparing common targets determined for additional drugs with similar therapeutic effects, targets mediating the side-effects of the drug of interest effects can be more certainly identified. Optionally, a more target-specific derivative of the drug of interest can be identified by next applying the previous described steps for improving the specificity of the drug of interest in order to eliminate the targets mediating the side-effects.

When the cell in which the test is carried out is a non-human eukaryotic cell, e.g., a yeast cell, it is often possible to extrapolate from the effects of the drug in the non-human cell to the effect in the human cell. This is due, in part, to the fact that a large proportion of genes are conserved in eukaryotes. As noted above, almost half of the proteins identified as defective in human heritable diseases show amino acid similarity to yeast proteins. It has also been reported that about 80% of all genes known to cause human disease have homologs in *C. elegans* ("Experts gather to discuss technologies being developed for functional genomic analysis," *Genetic Engineering News:*16, Nov. 15, 1996).

Certain particular embodiments of this invention will now be described in greater detail in the following sections.

5.3 Transcriptional State Embodiments

Embodiments based on measuring the transcriptional state are preferred. The transcriptional state can be measured by techniques of hybridization to arrays of nucleic acid or nucleic acid mimic probes, described in the next subsection, or by other gene expression technologies, described in the subsequent subsection. However measured, the result is a perturbation pattern including values representing RNA abundance ratios, which usually reflect DNA expression ratios (in the absence of differences in RNA degradation rates).

5.3.1 Transcript Arrays

The measurement of the transcriptional state by hybridization to transcript arrays is described in this subsection. In general, since such arrays have a natural physical arrangement, namely the arrangement of the probe nucleic acids on a surface, in this embodiment, the terms "perturbation pattern", "perturbation array", and "transcript array" are naturally used interchangeably.

Transcript Arrays Generally

In a preferred embodiment the present invention makes use of "transcript arrays" (also called herein "microarrays"). Transcript arrays can be employed for analyzing the transcriptional state in a cell, and especially for comparing the transcriptional states of two cells, such as a first cell that has been exposed to a drug and a second cell that has not been drug-treated, or a first cell in which a single gene has been disrupted and a second cell in which the gene has not been disrupted, or a first cell in which a single protein abundance has been changed and a second cell in which the protein abundance has not been changed, and so forth.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells, e.g., a cell exposed to a drug and a cell of the same type not exposed to the drug, are hybridized to the binding sites of the microarray. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the drug-treated cell will fluoresce green when the fluorophore is stimulated and the cDNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, *Science* 270:467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated and untreated cell.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, *Science* 274:546–567, which is incorporated by reference in its entirety for all purposes). In contrast, the human genome is estimated to contain approximately $10^5$ genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, *PCR Protocols: A Guide to Methods and Applications*, Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14:5399–5407; McBride et al., 1983, *Tetrahedron Lett.* 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29:207–209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270:467–470. This method is especially useful for preparing microarrays of cDNA. See also DeRisi et al., 1996, Use of a cDNA microarray to analyze gene expression patterns in human cancer, *Nature Genetics* 14:457–460; Shalon et al., 1996, A DNA microarray system for analyzing complex DNA samples using two-color fluorescent probe hybridization, *Genome Res.* 6:639–645; and Schena et al., 1995, Parallel human genome analysis; microarray-based expression of 1000 genes, *Proc. Natl. Acad. Sci. USA* 93:10539–11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767–773; Pease et al., 1994, Light-directed oligonucleotide arrays for rapid DNA sequence analysis, *Proc. Natl. Acad. Sci. USA* 91:5022–5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bioelectronics* 11: 687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids Res.* 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly(A)+ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–299). Poly(A)+ RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see e.g., Klug and Berger, 1987, *Methods Enzymol.* 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, *Nature Biotech.* 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, *Gene* 156:207; Pietu et al., 1996, Novel gene transcripts preferentially expressed in human muscles revealed by quantitative hybridization of a high density cDNA array, *Genome Res.* 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 ml dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™ II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, *Proc. Natl. Acad. Sci. USA*, 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, *Genome Research* 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, *Genome Res.*

6:639–645 and in other references cited herein. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event. According to the method of the invention, the relative abundance of an mRNA in two cells or cell lines is scored as a perturbation (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 3-fold to about 5-fold, but more sensitive methods are expected to be developed.

In some cases, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

Preparation of Transcript Arrays—RNA Sources

In one embodiment of the invention, transcript arrays reflecting the transcriptional state of a cell of interest are made by hybridizing a mixture of two differently labeled probes each corresponding (i.e., complementary) to the mRNA of a different cell of interest, to the microarray. According to the present invention, the two cells are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed). In the case of wild-type drug transcript arrays, the probes correspond to RNA isolated from (i) wild-type cells exposed to a drug and (ii) wild-type cells not exposed to drug. In the case of a modified cell transcript array, the probes correspond to RNA from (i) a wild-type cell and (ii) a cell which has been modified at the genetic, RNA, protein abundance, or protein activity levels. In the case of a genetic modification, the gene may be deleted or over-expressed. In the case of a modified cell drug transcript array the cDNA is made from (i) a modified cell (i.e., a genetic deletion mutant or a genetic over-expression mutant) exposed to a drug and (ii) a modified cell not exposed to a drug.

Drug Transcript Arrays

To prepare drug transcript arrays, the cells are exposed to the drug or drug candidate of interest. When the cells are grown in vitro, the compound is usually added to their nutrient medium. The amount of drug added and the length of exposure will depend on the particular characteristics of the drug, but usually will be between about 1 ng/ml and 100 mg/ml. In some cases a drug will be solubilized in a solvent such as DMSO.

5.3.2 Other Methods

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487).

5.4 Measurement of Alternative Aspects of Biological State

In various embodiments of the present invention, aspects of the biological state other than the transcriptional state, such as the translational state, the activity state, or mixed aspects can be measured. Details of these embodiments are described in this section.

Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array. and their binding is assayed with assays known in the art.

Alternatively, proteins can be separated by two-dimensional gel electrophoresis systems Two-dimensional gel electrophoresis is well-known in the art and typically involves iso-electric focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al., 1996, *Proc. Nat'l Acad. Sci. USA* 93:1440–1445; Sagliocco et al., 1996, *Yeast* 12:1519–1533; Lander, 1996, *Science* 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Embodiments Based on Other Aspects of the Biological State

Although monitoring cellular constituents other than mRNA abundances currently presents certain technical difficulties not encountered in monitoring mRNAs, it will be apparent to those of skill in the art that the use of methods of this invention, including application of various known methods of cell modification (such as deletion mutants and/or over-expression mutants), are applicable to any cellular constituent that can be monitored.

In particular, where activities of proteins relevant to the characterization of drug targets can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the perturbation patterns analyzed by the foregoing methods of this invention.

In alternative and non-limiting embodiments, perturbation patterns may be formed of mixed aspects of the biological state of a cell. A perturbation pattern can be constructed from, e.g., changes in certain mRNA abundances, changes in certain protein abundances, and changes in certain protein activities.

5.5 Cellular Modification Methods

Methods for targeted cellular modification at various levels of a cell are increasingly widely known and applied in the art. Any such methods that are capable of specifically targeting and altering (e.g., either by increase or activation or by decrease or inhibition) specific cellular constituents (e.g., gene expression, RNA concentrations, protein abundances, protein activities, or so forth) can be employed in constructing the modified-cell perturbation patterns and the modified-cell drug perturbation patterns of this invention. Preferable methods are capable of individually targeting each of a plurality of cellular constituents and most preferably a substantial fraction of such cellular constituents.

Modifications are preferably arranged to be "saturating." In the case of decreasing abundances or inhibiting activities, a modification is preferably arranged to decrease the particular cellular constituent or its activity to such an extent that all targets for action of that cellular constituent are essentially unsaturated or unbound. For example, it is preferable that all the mRNA encoding a protein species, or all of the encoded protein species itself, be eliminated from the cell, such as by deletion of the gene encoding the protein species. In the case of increasing abundances or activities, a modification is preferably arranged to increase the cellular constituent present in a cell to such an extent that all targets for action of the cellular constituent are essentially saturated or bound. Saturating modifications are preferable because the perturbation values resulting in the modified-cell perturbation patterns and the modified-cell drug perturbation patterns are extreme, thereby facilitating analysis and comparison of these patterns with increased statistical reliability (experimental noise and biases are relatively smaller).

In the following subsections certain preferred and alternative methods of cellular modification are described.

5.5.1 Genetic Modification

Genetically modified cells, i.e., mutant cells, can be made using cells of any organism for which genomic sequence information is available and for which methods are available that allow deletion (including disruption) of specific genes, or over-expression of specific genes. The genetically modified cells are used to make mutant transcript arrays and mutant drug transcript arrays. Preferably, a compendium is constructed that includes transcript arrays that represent the transcriptional states of each of a plurality of differently mutated mutant cells, e.g., a set of cells in which a separate cell is genetically modified. Such a compendium is advantageous to identify drug targets in a systematic and automatable manner. Preferably, the compendium includes mutant transcript arrays corresponding to at least about 30% of the protein coding genes in the subject organism, more preferably at least about 50%, still more preferably at least about 70%, even more preferably at least about 90%, most preferably at least about 95% or more, such as 98% of the protein coding genes. Preferably, the compendium includes mutant transcript arrays for the genes likely to be related to the action of drugs of interest. Genome sequencing is underway for several eukaryotic organisms, including humans, nematodes, *Arabidopsis*, and flies. Alternately, mutant transcript arrays and mutant drug transcript arrays can be produced as indicated without the need to construct a compendium.

In a preferred embodiment, the invention is carried out using a yeast, with *Saccharomyces cerevisiae* most preferred because the sequence of the entire genome of a *S. cerevisiae* strain has been determined. In addition, well-established methods for deleting or otherwise disrupting or modifying specific genes are available in yeast. It is believed that most (approximately four-fifths) of the genes in *S. cerevisiae* can be deleted, one at a time, with little or no effect on the ability of the organism to reproduce. Another advantage is that biological functions are often conserved between yeast and humans. For example, almost half of the proteins identified as defective in human heritable diseases show amino acid similarity to yeast proteins (Goffeau et al., 1996, Life with 6000 genes. *Science* 274:546–567). A preferred strain of yeast is a *S. cerevisiae* strain for which yeast genomic sequence is known, such as strain S288C or substantially isogeneic derivatives of it (see, e.g., *Nature* 369, 371–8 (1994); *P.N.A.S.* 92:3809–13 (1995); *E.M.B.O. J.* 13:5795–5809 (1994), *Science* 265:2077–2082 (1994); *E.M.B.O. J.* 15:2031–49 (1996), all of which are incorporated herein. However, other strains may be used as well. Yeast strains are available from American Type Culture Collection, Rockville, Md. 20852. Standard techniques for manipulating yeast are described in C. Kaiser, S. Michaelis, & A. Mitchell, 1994, *Methods in Yeast Genetics: A Cold Spring Harbor Laboratory Course Manual*, Cold Spring Harbor Laboratory Press, New York; and Sherman et al., 1986, *Methods in Yeast Genetics: A Laboratory Manual*, Cold Spring Harbor Laboratory, Cold Spring Harbor. N.Y., both of which are incorporated by reference in their entirety and for all purposes.

Construction of Deletion and Over-Expression Mutants in Yeast

In a preferred embodiment of the invention, yeast cells are used. In one embodiment, yeast genes are disrupted or deleted using the method of Baudin et al., 1993, A simple and efficient method for direct gene deletion in *Saccharomyces cerevisiae, Nucl. Acids Res.* 21:3329–3330, which is incorporated by reference in its entirety for all purposes. This method uses a selectable marker, e.g., the KanMx gene, which serves in a gene replacement cassette. The cassette is transformed into a haploid yeast strain and homologous recombination results in the replacement of the targeted gene (ORF) with the selectable marker. In one embodiment, a precise null mutation (a deletion from start codon to stop codon) is generated. Also see, Mach et al., 1994, New heterologous modules for classical or PCR-based gene disruptions in *Saccharomyces cerevisiae, Yeast* 10:1793–1808; Rothstein, 1991, *Methods Enzymol.* 194:281 each of which is incorporated by reference in its entirety for all purposes. An advantage to using precise null mutants is that it avoids problems with residual or altered functions associated with truncated products. However, in some embodiments (e.g., when investigating potential targets in the excluded set, Section 5.6, infra) a deletion or mutation affecting less than the entire protein coding sequence, e.g., a deletion of only one domain of a protein having multiple domains and multiple activities, is used.

In some embodiments, the polynucleotide (e.g., containing a selectable marker) used for transformation of the yeast includes an oligonucleotide marker that serves as a unique identifier of the resulting deletion strain as described, for example, in Shoemaker et al., 1996, *Nature Genetics* 14:450. Once made, disruptions can be verified by PCR using the internal KanMx sequences, or using an external primer in the yeast genome that immediately flanks the disrupted open reading frame, and assaying for a PCR product of the expected size. When yeast is used, it may sometimes be advantageous to disrupt ORFs in three yeast strains, i.e., haploid strains of the a and α mating types, and a diploid strain (for deletions of essential genes).

Over-expression mutants are preferably made by modifying the promoter for the gene of interest, usually by replacing the promoter with a promoter other than that naturally associated with the gene, such as an inducible promoter. In addition, or alternatively, an enhancer sequence can be added or modified. Other methods for carrying out genetic modification to increase expression from a predetermined gene are well known in the art, and include expression from vectors, such as plasmids, carrying the gene of interest.

Construction of Mutants in Other Organisms

The method of the present invention can be carried out using cells from any eukaryote for which genomic sequence of at least one gene is available, e.g., fruit flies (e.g., *D. melanogaster*), nematodes (e.g., *C. elegans*), and mammalian cells such as cells derived from nice and humans. For example, more than 60% of the *C. elegans* genome has been sequenced ("Experts gather to discuss technologies being developed for functional genomic analysis," *Genetic Engineering News:*16, Nov. 15, 1996). Methods for disruption of specific genes are well known to those of skill in the art, see, e.g., Anderson, 1995, Methods Cell Biol. 48:31; Pettitt et al., 1996, Development 122:4149–4157; Spradling et al., 1995, Proc. Natl. Acad. Sci. USA; Ramirez-Solis et al., 1993, Methods Enzymol. 225:855; and Thomas et al., 1987, Cell 51:503, each of which is incorporated herein by reference in its entirety for all purposes.

5.5.2 Other Methods

Other known methods of cellular modification target RNA abundances or activities, protein abundances, or protein activities. Examples of such methods are described in the following.

Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334: 585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15: 287–299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. tDNA genes (i.e., genes encoding tRNAs) are useful in this application because of their small size, high rate of transcription, and ubiquitous expression in different kinds of tissues. Alternately, an inducible promoter (e.g., a glucocorticoid or a tetracycline response element) can by used so that ribozyme expression can be selectively controlled. Therefore, ribozymes can be routinely designed to cleave virtually any mRNA sequence, and a cell can be routinely transformed with DNA coding for such ribozyme sequences such that a catalytically effective amount of the ribozyme is expressed. Accordingly the abundance of virtually any RNA species in a cell can be essentially eliminated.

In another embodiment, activity of a target RNA (preferable mRNA) species, specifically its rate of translation, is inhibited by use of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered to a cell or which can be produced intracellularly by transcription of exogenous, introduced sequences in quantities sufficient to inhibit translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

In an alternative embodiment, the antisense nucleic acids of the invention are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Such promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Therefore, antisense nucleic acids can be routinely designed to target virtually any mRNA sequence, and a cell can be routinely transformed with or exposed to nucleic acids coding for such antisense sequences such that an effective amount of the antisense nucleic acid is expressed. Accordingly the translation of virtually any RNA species in a cell can be inhibited.

Finally, in a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species increases (or decreases) the abundance of that species. Methods for controllably increasing the degradation rate of a target protein in response to elevated temperature or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation is blocked by exposure methotrexate. This method is adaptable to other N-terminal degrons which are responsive to other inducing factors, such as drugs and temperature changes.

Target protein abundances and also, directly or indirectly, their activities can also be decreased by (neutralizing) antibodies. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al, 1995, Trends in Cell Biology 5:248–252). A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering* (vol. 2) (Borrebaeck ed.), pp 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as *bacillus* Calmette-Guerin (BCG) and *corynebacterium parvum*.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, in *Monoclonal Antibodies and Cancer Therapy*, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to 1012 different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, Science 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the $F(ab')_2$ fragment which can be produced by pepsin digestion of the antibody molecule; the Fab' fragments that can be generated by reducing the disulfide bridges of the $F(ab')_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

Methods of Modifying Protein Activities

Methods of directly modifying protein activities include, inter alia, dominant negative mutations, specific drugs (used in the sense of this application), and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, over expression of an inactive form can cause competition for natural substrates or ligands sufficient to significantly reduce net activity of the target protein. Such over expression can be achieved by, for example, associating a promoter of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be decreased by expression of genes coding exogenous protein fragments that bind to multimeric association domains and prevent multimer formation. Alternatively, over expression of an inactive protein unit of a particular type can tie up wild-type active units in inactive multimers, and thereby decrease multimeric activity (Nocka et al., 1990, The EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Finally, alternatively to techniques involving mutations, activities of certain target proteins can be altered by exposure to exogenous drugs or ligands. In a preferable case, a drug is known that interacts with only one target protein in the cell and alters the activity of only that one target protein. Exposure of a cell to that drug thereby modifies the cell. The alteration can be either a decrease or an increase of activity. Less preferably, a drug is known and used that alters the activity of only a few (e.g., 2–5) target proteins with separate, distinguishable, and non-overlapping effects.

5.6 Identification of Genetic Drug Targets

In this section, a detailed embodiment of the methods of this invention for comparison of perturbation patterns is presented. This detailed an embodiment is based on genetic modifications (e.g., gene disruption or gene over expression) and measurement of the transcriptional state of a cell. The result of these comparison methods is the identification of one or more direct targets of a drug. It will be immediately apparent that comparison methods of this detailed embodiment can be easily adapted to other embodiments of this invention based on other cellular modification methods and measurements of other aspects of the cellular biological state. The following description is directed to the preferred embodiment for convenience of presentation and language only. Further, based on the discoveries leading to this invention, the drug target identification according to this invention is not limited to the method described in this section. This method described herein is illustrative of one method for comparison. Certain variations are described below, and others will be apparent to those of skill in the art. This detailed embodiment is exemplified in Example 6.5.

Figure 2:
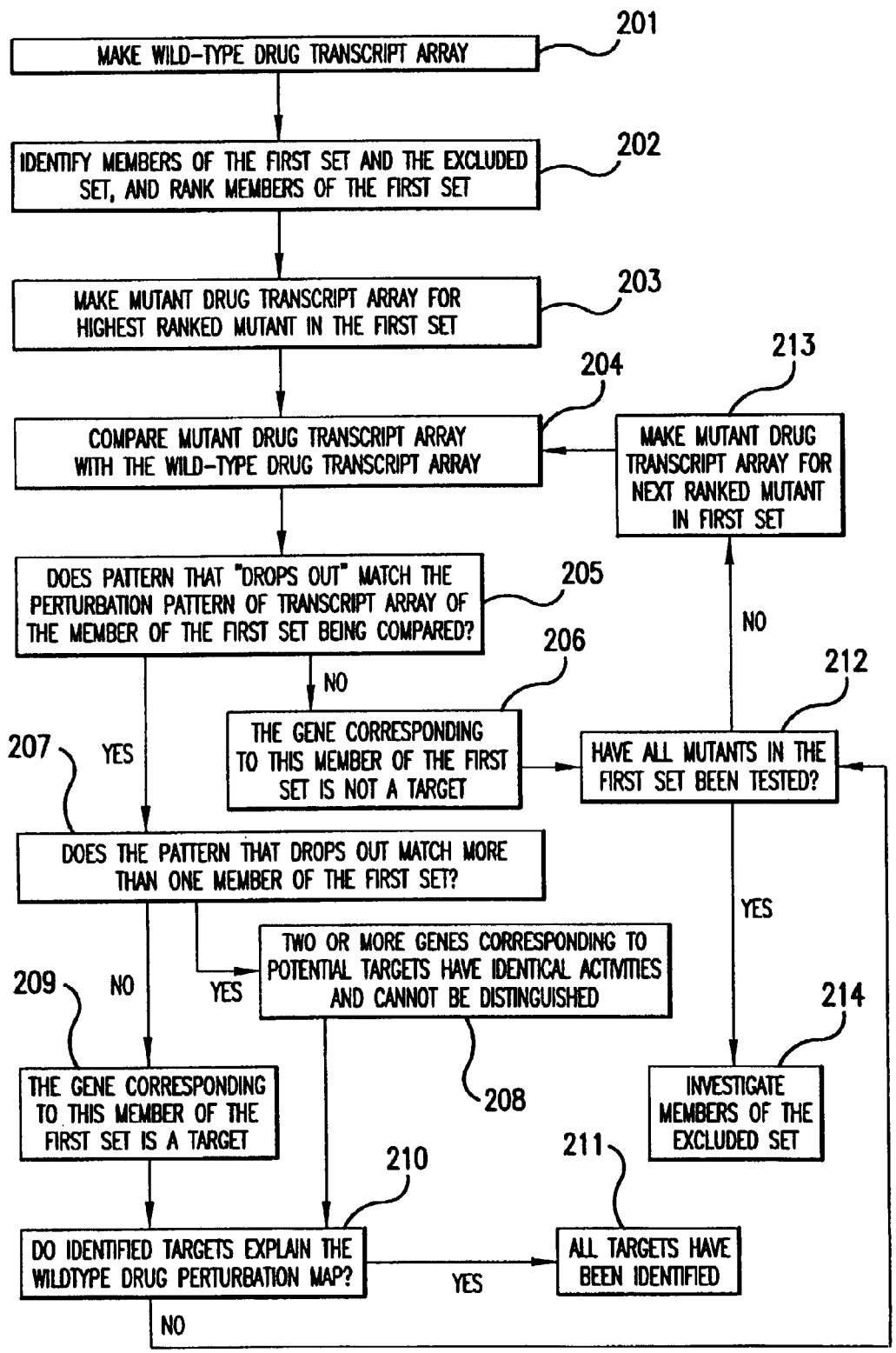
FIG. 2 is flow-chart summarizing steps in a method of identifying the targets of a drug.

The detailed embodiment of the transcriptional perturbation pattern (here preferably measured by transcript arrays) comparison methods is described with respect to FIG. 2. In step 201, a wild-type drug transcript array is made using the drug under investigation, and sites on the wild type drug transcript array exhibiting perturbations are identified. If there are no sites exhibiting perturbations, the drug is deemed to have no target (at the dosage and conditions of administration) and is not further investigated. If there are one or more sites of perturbation on the wild-type drug transcript array, each perturbation site is scored as a positive perturbation site (+) or a negative perturbation site (−), preferably by using the statistical tests described above. (Alternately, the magnitudes of the measured values can be directly compared.) The number of such perturbations (i.e., perturbation sites) on the wild-type drug transcript array is usually small compared to the number of genes in the genome of the cell being studied. Often it is less than about 10% of the number of genes in the subject genome, more often less than about 3%. Thus, for a yeast cell, the number of perturbation sites will usually be less than about 180 and for a human cell the number will usually be less than about 1500. However, for most drugs the number will be even smaller, usually less than about 100, and often less than about 20 or about 10 perturbation sites.

In succeeding step 202, mutant transcript arrays are examined, and those mutant transcript arrays that share at least one site of positive or negative perturbation (or have similar perturbation values) in common with a site in the wild-type drug transcript array are identified. This examination (and subsequent comparisons) can be systematically carried out using a library of cell mutants in which each mutant has been modified at a different genetic locus. Such a library can be used, in the first instance to construct a "compendium" of mutant transcript arrays for each cell mutant in the library. Where such a cell library and associated compendium are available, they are preferably, but optionally, employed in this step.

In determining what sites of perturbation are in common, the site(s) on the mutant transcript arrays corresponding to the mutated (e.g, deleted) gene are not considered. This is because a drug that changes the activity of a protein target will not necessarily change the abundance of transcripts that encode that protein, which abundance however will be changed by a gene disruption or over expression.

All the mutant transcript arrays so identified ("the complete set" of mutant transcript arrays) are next divided into a first set of mutant transcript arrays and an excluded set of mutant transcript arrays. A mutant transcript array that shares at least one site of positive or negative perturbation in common with a site in the wild-type drug transcript array (i.e., a member of the "complete set") is excluded, i.e., is a member of the excluded set, if it also has a site of perturbation that is not found in the wild-type drug transcript array. In making this determination the sites on each mutant transcript array corresponding to the mutated (e.g, deleted) gene are not considered. Conversely, a mutant transcript array is in the first set if all its sites and types of perturbation (the site corresponding to the mutated gene is again ignored in this comparison) are shared with the wild-type drug transcript array.

The potential genetic targets of the drug are those that "correspond" to the mutant transcript arrays of the first set and the excluded set. Most often the genetic target(s) are expected to be found in the first set. Although genes in the excluded set may also be direct targets of the drug, they typically encode multi-functional proteins. For example, a gene in the excluded set may encode a protein with two functional domains, one domain being a target of the drug and the other having other cellular effects. Thereby, deletion of such a gene will have certain effects shared with the drug and certain other effects not shared with the drug.

A potential target "corresponds" to a mutant transcript array when the mutant transcript array is made using RNA (e.g., cDNA) from a cell mutated at the target gene. For example, if RNA from a mutant in which "gene 5" is deleted (or over expressed) is used to make a mutant transcript array, the resulting mutant transcript array "corresponds" to gene 5. In addition, the mutant transcript array "corresponds" to the cell or cell line mutated at gene 5. As used herein, both the mutant cell and the corresponding mutant transcript array in this example can be referred to as "Δ5", meaning a change (e.g., deletion) at gene 5.

Finally, the mutant transcript arrays of the first set are ranked in order of similarity to the wild-type drug transcript array (from 1 to N, where N is the number of arrays in the first set and array number 1 is the array that most closely matches the wild-type drug transcript array). Ranking can be based on the total number of perturbation sites in common (i.e., found in both the mutant transcript array and the wild-type drug transcript array), with a mutant transcript array with a higher number of sites in common with a wild-type drug transcript array being ranked higher than one with a lower number of sites in common. When several mutant transcript arrays share an equal number of sites with the wild-type drug transcript array (i.e., equally ranked), they are given an arbitrary rank order for the purposes of analysis (as described infra). Alternatively, ranking can be based on the correlation coefficient of the wild-type drug transcript array and the mutant transcript array. Mutant transcript arrays are so ranked so that the higher the correlation coefficient the higher the rank of the array.

In step 203, a mutant drug transcript array is constructed using RNA (or cDNA synthesized therefrom) from the drug-exposed mutant cell that corresponds to the next highest ranked mutant transcript array not yet examined. The method preferably starts with mutant cells corresponding to the highest ranked mutant transcript array and proceeds down the rank order as more mutant drug transcript arrays need to be constructed and examined.

In step 204, the mutant drug transcript array is compared to the wild-type drug transcript array. To make this comparison, the perturbation pattern of the mutant drug transcript array is compared to the perturbation pattern of the wild-type drug transcript array. For each site of perturbation in the wild-type drug transcript array, it is determined whether there is the same (i.e., positive or negative) perturbation at the equivalent site on the mutant drug transcript array. If there is not, the site "drops out." The sites that "drop out" are collectively known as the "drop-out set" or pattern. If there is, the site "remains." The sites that "remain" are collectively known as the "remaining set" or pattern. Again, the site on the mutant drug transcript array to which the product of the mutated (e.g., deleted) gene binds is not considered in this embodiment (as explained above). As discussed above, sites drop out if the drug effect at that site is eliminated (or changed) in the mutant drug transcript array and remain if the mutation has no effect on drug action at that site. Previously described statistical tests can optionally be used to score and select the drop-out sites.

It will be recognized that the set of sites that "drop out" forms a pattern (the "drop-out pattern" or set), as does the set of the sites that remain (the "remaining" pattern or set). The drop-out pattern, including the position and direction (i.e., positive or negative) or value of each perturbation can be represented schematically, as in Example 6.5, mathematically or by some other means. Preferably, the perturbation direction or value for a site in the drop out pattern is obtained from the corresponding site in the mutant drug transcript array.

In step 205, the "drop-out pattern" (or, equivalently the drop-out set) is compared to the perturbation pattern of the mutant transcript array being examined. This comparison can be done by, e.g., one of the comparison options previously described. In one option, the two patterns are compared site by site, and are scored (preferably in view of statistical confidence intervals) as the same if they have the same perturbations, either in direction or in direction and value, and at the same sites. In another option, a correlation coefficient can be computed between the two patterns, and the patterns are scored as the same if the correlation coefficient is above some chosen statistical significance value.

In step 206, if the patterns are scored not to be the same, it is determined that the gene (or product of the gene, or activity of that product) corresponding to the mutant transcript array being currently examined is not a target of the drug. As above, the site on the mutant transcript array to which the product of the mutated (e.g., deleted) gene binds is not considered. In this case, the method progresses on to step 212 to select and process the next highest ranked mutant transcript array, if any.

If the patterns are determined to be the same in step 205, the method proceeds to step 207, where it is determined if the gene (or product of the gene, or activity of that product) corresponding to the mutant transcript array being currently examined is a direct target of the drug.

If the comparison at step 207 produces more than one possible match, the method proceeds to step 208, where further comparisons of the drop-out pattern (or set) are made with other transcript arrays in the first set of transcript arrays. In the case of a small number of drugs, the pattern of sites that drop out will be the same as more than one member of the first set. This occurs where two members of the first set have identical perturbation patterns, ignoring the sites corresponding to the mutated gene. In such a case, it will not be immediately possible by the methods of this invention to distinguish between (or even less often, among) the corresponding genes and determine which is a direct target of the drug.

After steps 208 and 209, step 210 determines whether all the direct targets of the drug have already been found. For many drugs it is not necessary to prepare mutant drug transcript arrays for all of the mutants corresponding to the transcript arrays of the first set. Instead, it will often be possible to ascertain, before proceeding through every target corresponding to the first set, that all of the drug's direct targets have been identified. If all the direct targets have been identified, the method has completed its task and ends at step 211.

All of a drug's targets have been found when the drop-out patterns for all of the identified targets can be combined to explain the wild-type drug perturbation pattern (i.e., the pattern of perturbations on the wild-type drug transcript array); that is, the mutant targets fully account for the effect of the drug on the wild-type cell by eliminating all drug effects when they are all mutated.

In the simple case in which the drug has only a single direct target, it will be appreciated that the perturbation pattern that drops out when the mutant drug transcript array corresponding to the target is compared to the wild-type drug transcript array will be the same as the wild-type drug transcript array. This case can be immediately and directly identified. Alternately, it will also be appreciated that, when the drug being investigated has a single target, the wild-type drug transcript array for that drug will exactly match a mutant transcript array in the compendium (ignoring the site corresponding to the mutated gene). If this is identified at an earlier step, this method can be completed at that step.

In another special case, it will be appreciated that the remaining pattern also provides information about the direct drug targets. For example, if, when the pattern that drops out identifies a target of the drug (e.g., a first target) and the pattern that "remains" is the same as a perturbation pattern for a mutant transcript array from the first set, the gene corresponding to that mutant transcript array is also a target (e.g., a second target). The drug has only these two targets.

In general cases of two or more identified direct targets, when the drop-out patterns for the identified targets do not overlap, the patterns can be combined by taking a simple set union of all the patterns. For example, a wild-type drug transcript array with positive perturbations at positions 1, 3, and 5 (arbitrarily numbered positions), negative perturbations at positions 2 and 4, and no perturbations at positions 6–6000 would be fully explained by a first target with a "drop-out pattern" showing positive perturbations at positions 1, 3, and 5 only and a second target with a "drop-out pattern" showing negative perturbations at positions 2 and 4 only.

When the drop-out patterns for the identified targets do overlap (or, equivalently, the drop-out sets intersect), the patterns are preferably combined in a more complex manner. In the previous case, it is not necessary to determine the magnitude of the perturbations in the drop-out patterns. Rather, it is sufficient to determine whether they are negative or positive (and thus match a negative or positive perturbation site on the wild-type drug transcript array). However, when there is a positive perturbation at a particular site in the drop-out pattern for one or more targets, and there is a negative perturbation at the same site in the drop-out pattern for one or more different targets, it is necessary, when adding or superimposing the drop-out patterns, to consider the magnitude of the perturbations. For example, the addition of a larger magnitude negative perturbation and a smaller magnitude positive perturbation are scored as matching a negative perturbation in the wild-type drug transcript array. Similarly, the addition of a larger magnitude positive perturbation and a smaller magnitude negative perturbation is scored as matching a positive perturbation in the wild-type drug transcript array. In the case, described supra in which two or more members of the first set have identical perturbation patterns, only one pattern is used in adding (the magnitude of) perturbation sites (e.g, when a positive site is added to a negative site).

If it is determined that further targets remain to be identified, in step 212 the method checks whether there are more mutant transcript arrays in the first set. If so, in step 213, a mutant drug transcript array is made for the next highest ranked mutant transcript array. In further repetitions, the preceding steps are repeated using the second highest ranked mutant transcript array, and so on through the transcript arrays of the first set.

If all of the members of the first set have been analyzed or interrogated (i.e., the transcript arrays of the first set have been exhausted), and not all of the targets have been identified, it is necessary, at step 214, to investigate members of the excluded class. This may occur in cases in which a drug affects a single activity of a protein that has multiple activities (e.g., located in different domains of the protein). In these comparatively less common cases, further analysis can be carried out by making deletion mutants in which only a portion of the protein coding sequence (e.g., corresponding to a single protein domain) is mutated (e.g., deleted) in each mutant, and using mutant drug transcript arrays corresponding to those mutants for analysis.

It will be recognized that these steps can be varied and some may be omitted. For example, it is advantageous to rank the members of the first set (step 202) because this will reduce the number of mutant drug transcript arrays that must be produced in those cases in which it is not necessary to investigate all of the members of the first class. However, it is also possible to make mutant drug transcript arrays from all members of the first class simultaneously, or to rank and process them in an order other than the rank order described above.

As already noted supra, the above described embodiment of the comparison methods of this invention is provided for illustration and not limitation. Those of skill in the art will recognize that variations, such as variations arising from the use of computer software for comparison and pattern recognition, may be made in the method. It will be clear to one of skill in the art that it will be advantageous to use computers to make comparisons such as those discussed supra.

A further variation is the use of statistical methods, including use of correlation coefficients (as described above) preferably computed from the base-10 logarithm of the expression ratios (or perturbation ratios), to compare perturbation patterns in general and transcript arrays in particular. In this variation, cellular constituents can be scored as "perturbed" or as "not perturbed" according to a confidence value derived from the distribution of data values. For example, a constituent can be scored as perturbed if the magnitude of its change is less than 5% (or 1%, or 10%, or 20%) likely to be due to chance. Thereby, patterns of perturbed values can be found and compared to determine patterns of constituents that drop out or remain. Alternatively, such scoring is not done.

Further perturbation patterns, either measured or derived, can be compared by computing their correlation coefficient. Similarly to individual constituents, patterns can be scored for "difference" or "identity." Two patterns are scored as different if their correlation coefficient is less than 0.1% (or 0.5%, or 1%, or 5% or 10% of 20%) likely to be due to chance. For example, a drop-out pattern can be said to be identical to a mutant pattern if the correlation coefficient of their perturbation patterns is less than 0.1% likely to be due to chance.

6 EXAMPLES

The following examples are presented by way of illustration of the previously described invention and are not limiting of that description.

6.1 Synthesis of Labeled cDNA

This example describes the synthesis of labeled cDNA from yeast cells. Yeast (*Saccharomyces cerevisiae*) cells were grown in YAPD at 30° C. to an $OD_{600}$ of 1.0 (±0.2), and total RNA prepared by breaking cells in phenol/chloroform and 0.1% SDS by standard procedures (Ausubel et al., 1995, Current Protocols in Molecular Biology, Greene Publishing and Wiley-Interscience, New York, Ch. 13).

Poly(A)$^+$ RNA was selected by affinity chromatography on oligo-dT cellulose (New England Biolabs) essentially as described in Sambrook et al. (Molecular Cloning—A Laboratory Manual (2nd Ed.), Vol. 1, Cold Spring Harbor Laboratory, Cold Spring Harbor, N.Y., 1989). First strand cDNA synthesis was carried out with 2 µg poly(A)$^+$ RNA and Superscript™ II reverse transcriptase (Gibco-BRL) according to the manufacturer's instructions with the following modifications. Deoxyribonucleotides were present at the following concentrations: dA, dG, and dC at 500 µM each, dT at 100 µM and either Cy3-dUTP or Cy5-dUTP (Amersham) at 100 µM. cDNA synthesis reactions were carried out at 42–44° C. for 90 minutes, after which RNA was degraded by the addition of 2 units of RNAse H, and the cDNA products were purified by two successive rounds of centrifugation dialysis using MICROCON-30 microconcentrators (Amicon) according to the manufacturer's recommendations.

6.2 Production of Yeast Genome Microarrays

Double-stranded DNA polynucleotides corresponding in sequence to each ORF in the *S. cerevisiae* genome encoding a polypeptide greater than 99 animo acids (based on the published yeast genomic sequence, e.g., Goffeau et al., 1996, *Science* 274:546–567) are made by polymerase chain reaction (PCR) amplification of yeast genomic DNA. Two PCR primers are chosen internal to each of the ORFs according to two criteria: (i) the amplified fragments are 300–800 bp and (ii) none of the fragments have a section of more than 10 consecutive nucleotides of sequence in common. Computer programs are used to aid in the design of the PCR primers. Amplification is carried out in 96 well microtitre plates. The resulting DNA fragments are printed onto glass microscope slides using the method of Shalon et al., 1996, *Genome Research* 6:639–645.

6.3 Making Yeast Deletion Mutants

*S. cerevisiae* deletion mutants are made for each ORF encoding a polypeptide greater than 99 amino acids in length, based on the published yeast genomic sequence (see, Goffeau et al., 1996, *Science* 274:546–567).

The yeast genes are disrupted according to the method of Baudin et al. (*Nucl. Acids Res.* 21:3329–3330, 1993) using the KanMx gene (gentamicin resistance) as the selectable marker. The gene replacement cassette is amplified as a fragment that contains 45 base pairs of sequence both upstream and downstream of the open reading frame to be disrupted, allowing precise replacement of target open reading frame from the initiation of start codon through the translational stop signal by using simple yeast transformation. Each of the disruptions is validated by PCR.

6.4 Preparing Transcript Array Compendium

Labeled cDNA is prepared as described in Example 6.1, using wild-type yeast cells and the yeast deletion mutants described in Example 6.3. Fluorescently-labeled cDNAs (2–6 µg) are resuspended in 4×SSC plus 1 µg/µl tRNA as carrier and filtered using 0.45 µM filters (Millipore, Bedford, Mass.). SDS is added to 0.3%, prior to heating to 100° C. for 2 minutes. Probes are cooled and immediately hybridized to the microarrays produced as described in Example 6.2, for 4 hours at 65° C. Non-hybridized probe is removed by washing in 1×SSC plus 0.1% SDS at ambient temperature for 1–2 minutes. Microarrays are scanned with a fluorescence laser-scanning device as previously described (Schena et al., Science 270:467–470, 1995; Schena et al., 1995, Proc. Natl. Acad. Sci. USA 93:10539–11286) and the results (including the positions of perturbations) are recorded.

6.5 Identification of Genetic Target of a Drug

This example describes the identification of the genetic target of a candidate drug in yeast. 1 mg/ml of Drug A is added to the culture medium of wild-type S. cerevisiae and incubated at 37° C. for 2 hours.

RNA isolated from the drug-treated cells and from wild-type cells not exposed to the drug is reverse transcribed into differently labeled cDNA as described in Example 6.1. Equal amounts by weight of the differently labeled cDNA from the drug-treated and untreated cells are mixed and hybridized to the cDNA microarray described in Example 6.2, using the conditions described in Example 6.4. The resulting wild-type drug transcript array is scanned and results analyzed as described in Example 6.4. The results are presented schematically in FIGS. 3A–3L. For purposes of illustration, 9 of the roughly 6000 sites on the microarray are schematically represented. The sites are numbered as shown in FIG. 4A, with each numbered site corresponding to a hybridization site for the product of a similarly named gene (i.e., gene 1, gene 2, gene 3, etc.). The key to interpreting the perturbations is shown in FIG. 4B. The site on a mutant drug transcript array corresponding to a deleted gene will show no hybridization, because neither the drug-treated deletion cells nor the non-treated deletion cells that contribute RNA (e.g., cDNA) to the hybridization mixture express transcripts corresponding to the deleted gene. This absence of hybridization is indicated by X. A blank area in a site on the diagram indicates no perturbation.

The perturbations evident in the wild-type drug transcript array for Drug A are shown in FIG. 3A. The wild-type drug transcript array shows perturbations at sites 3, 4, 6 and 8. The compendium of mutant transcript arrays (i.e., deletion compendium), of which 9 selected mutant transcript arrays are shown in FIG. 3B, is scanned and the deletion mutants having a perturbation in common with the wild-type drug transcript array are identified. The arrays so identified are the arrays corresponding to mutants deleted at gene 1 (Δ1), gene 2 (Δ2), gene 3 (Δ3), gene 5 (Δ5), and gene 7 (Δ7). (In each mutant transcript array, the site corresponding to the deleted gene is not considered.)

The Δ5 mutant transcript array is placed in the excluded set because it has a site (other than a position corresponding to the deleted gene) of perturbation that is not found in the wild-type drug transcript array (i.e., at positions 7 and 9). Thus, the first set is Δ1, Δ2, Δ3, and Δ7.

The arrays of the first step are ranked as follows: Δ1, Δ2 and Δ7 each have two perturbations in common (not counting the site corresponding to the deleted gene) and are ranked in an arbitrary order (1, 2, 7). Δ3 has one perturbation in common with the wild-type drug transcript array, and is thus lower ranked.

Because Δ1 is the highest ranked member of the first set, a mutant drug transcript array is prepared using RNA from cells mutated at gene 1. A Δ1 mutant drug transcript array is prepared using RNA from Δ1 deletion strain cells exposed to Drug A, and similar cells not exposed to Drug A (FIG. 3C). The mutant drug array is compared to the wild-type drug transcript array as shown in FIG. 3D. FIG. 3E shows the perturbation pattern for the sites that "drop out." No sites drop out for gene 1. The perturbation pattern for the sites that drop out is compared to the mutant transcript array from the member of the first set being investigated (i.e., the Δ1 mutant transcript array; see FIG. 3B). In this case it does not match, indicating that gene 1 is not a target of drug A.

The analysis is then repeated for the next (i.e., second) ranked member of the first set (i.e., Δ2). A mutant drug transcript array is made for Δ2 (FIG. 3F) and compared to the wild-type drug transcript array (FIG. 3G). The perturbation pattern of the sites that "drop out" (FIG. 3H), is compared to the mutant transcript array from the member of the first set being investigated (i.e., the Δ2 mutant transcript array; see FIG. 3B). In this case it matches, indicating that gene 2 is a target of Drug A.

Since a target has been identified, it is possible to determine whether there are additional targets for Drug A. The drop-out pattern for the Δ2 mutant drug transcript array (FIG. 3H) is considered in isolation since there are no other targets yet identified. The drop-out pattern for the Δ2 mutant drug transcript array does not produce the perturbation pattern for the wild-type drug transcript array (FIG. 3A). Therefore, it is concluded that there are additional targets.

The analysis is then repeated for the next (i.e., third) ranked member of the first set (i.e., Δ7). A mutant drug transcript array is made for Δ7 (FIG. 3I) and compared to the wild-type drug transcript array (FIG. 3J). The perturbation pattern of the sites that "drop out" (FIG. 3K), is compared to the mutant transcript array from the member of the first set being investigated (i.e., the Δ7 mutant transcript array; see FIG. 3B). In this case it matches, indicating that gene 7, along with gene 2, is a target of Drug A.

Since a second target has been identified, it is possible to determine whether there are additional targets for Drug A. The drop-out pattern for the Δ2 mutant drug transcript array (FIG. 3H) is combined with (i.e., added to or superimposed with) the drop-out pattern for the Δ7 mutant drug transcript array (FIG. 3K). The combination produces the perturbation pattern for the wild-type drug transcript array (FIG. 3L).

Thus, genes 2 and 7 are identified as the only direct targets of Drug A.

The diagram in FIG. 4C shows a relationship between Drug A and genes 1–9 which accounts for the results found in this example. Drug A is an inhibitor of the proteins encoded by genes 2 and 7. Gene 5 is an activator of genes 7 and 9. Gene 2 is an inhibitor of genes 4 and 8. Genes 7 and 1 are activators of gene 3; gene 3 is an activator of gene 6; and gene 1 activates itself. As used herein, a first gene may be described as "activating" or "inhibiting" a second gene when the first gene, or expression of any product of the first gene, changes the abundance of an RNA transcript encoded by the second gene, without regard to the mechanism by which this change is effected.

6.6 Identification of Calcineurin as a FK506 Target 6.6.1 Cyclosporin and FK506

Cyclosporin A ("CSA") and FK506 are drugs with reasonably well-characterized effects in yeast, plant and mammalian cells (see, generally, Cardenas et al., 1994, Perspectives In Drug Discovery and Design 2:103–126). CSA, a cyclic undecapeptide, and FK506, a macrolide, are used clinically as immunosuppressants to prevent graft rejection following organ transplantation. Despite being chemically unrelated, both drugs are known to exert their immunosuppressive effects by inhibiting the same intermediate step of the calcium-dependent signalling pathway, activation of the calcium- and calmodulin-dependent serine-threonine protein phosphatase, calcineurin, and thereby block release of resting T-cells from G0 arrest.

FK506 and CSA have an analogous action in yeast, in that both drugs prevent the calcium- and calcineurin-dependent release from a cell cycle arrest. Calcineurin, a heterodimeric type 2B phosphatase composed of a regulatory component (encoded by CNB1) and a catalytic subunit (encoded by two nearly identical genes, CNA1 and CNA2) (collectively called herein "CNA"), is not essential in yeast, but is required for cells to overcome mating-factor induced arrest (see, e.g., Stathopoulos et al., 1997, Genes and Development 11:3432–3444; Matheos et al., Genes and Development 11:3445–3458). Each of the two mating types of yeast normally secrete a mating factor that arrests cells of the opposite mating type in G1 phase, preparing them for mating and subsequent karyogamy. In the absence of cells of the opposite mating type, however, cells arrested by a mating factor will eventually adapt to its presence and bypass the arrest in a calcium and calcineurin-dependent manner. Both immunosuppressants block this adaptation step by inhibiting calcineurin.

CSA and FK506 have been found to require intracellular receptor proteins (generally called immunophilins) to mediate their inhibitory effects on calcineurin. The family of CSA receptor proteins are called cyclophilins; and the family of FK506 binding proteins are called FKBPs. While the cyclophilin and FK506 binding protein families share little sequence similarity, all are proline isomerases whose enzymatic activity is potently inhibited when bound by the respective immunosuppressant.

Seven cyclophilins have been identified in S. cerevisiae, yet in yeast strains that are sensitive to CSA, disruption of the most abundant cyclophilin, CPH1, completely suppresses CSA-mediated growth inhibition, suggesting that most of the effects of CSA is mediated through CPH1. Conversely, four FKBPs proteins are present in yeast, and even deletion of all four genes does not fully suppress FK506-mediated growth inhibition, suggesting that other gene products that interact with FK506 significantly contribute to its effects. FPR1 is the most abundant cytoplasmic member of the FKBP protein family.

6.6.2 Production of Transcript Arrays

Wild-type drug transcript arrays, mutant transcript arrays and mutant drug transcript arrays were produced by the following methods for the drugs CSA and FK506 and for cells disrupted for the gene cna, cph1, and fpr1.

To produce the wild-type drug transcript arrays, a wild-type S. cerevisiae strain was grown in the presence or absence of either 1 mg/ml FK506 or 30 mg/ml CSA for three generations prior to harvesting the cells and isolating polyA+ RNA. The RNA was converted into cDNA while simultaneously incorporating fluorescent nucleotides, according to standard protocols as described above. The cDNAs were hybridized to either a microarray having 140 sites with relevant S. cerevisiae ORF sequences, or to a microarray having sites with 5900 sites with nearly all known S. cerevisiae ORF sequences. The intensities of the two fluors used to label the RNAs to be compared were measured at each site of the array. The ratio of these intensities is referred to as the expression ratio. By this method wild-type drug transcript arrays for the drugs FK506 and CSA were produced.

To produce deletion mutant transcript arrays, RNA was prepared from a publicly available S. cerevisiae strain that contains genetic disruptions in both catalytic subunits of calcineurin (hereinafter, the cna mutant) and its isogeneic with the parental wild-type strain. These two strains were grown in parallel, harvested and processed in an identical manner as described above. As above, the cDNAs were hybridized to the array and the intensities of the two fluors (expression ratio) were measured at each site of the array. Thereby a cna mutant transcript array was produced.

Deletion mutant transcript arrays were also produced in similar manners for disruptions to the genes cph1 (coding the major cyclophilin in yeast) and fpr1 (coding the major FK506-binding protein).

To produce deletion mutant drug transcript arrays, the cna, cph1, or fpr1 deletion strains were grown in the presence or absence of either 1 mg/ml FK506 or 30 mg/ml CSA for three generations prior to harvesting the cells and isolating polyA+ RNA. cDNAs were prepared and hybridized to the array as described supra and the intensities of the two fluors were measured. By this method the following mutant drug transcript arrays were produced: a cna mutant FK506 drug transcript array, a cph1 mutant FK506 drug transcript array, a fpr1 mutant FK506 drug transcript array, a cna mutant CSA drug transcript array, a cph1 mutant CSA drug transcript array, a fpr1 mutant CSA drug transcript array, a cna mutant FK506 drug transcript array, a cph1 mutant FK506 drug transcript array, and a fpr1 mutant drug FK506 drug transcript array.

Selected pairs of the transcript arrays were compared by computing a correlation coefficient between the pairs as previously described. As is known in the art, higher values of the correlation coefficient represent a greater degree of similarity between the pair of arrays. As indicated subsequently, in some cases expression ratios were directly used for this computation, while in other cases the $\log_{10}$ function of the expression ratios were used.

6.6.3 Targets of Cyclosporin and FK506

Wild-type drug transcript arrays for FK506 and CSA, mutant transcript arrays for cna, cph1 and fpr1, and mutant drug transcript arrays for these drugs and mutants were prepared by hybridizing to a microarray with sites having approximately 5900 S. cerevisiae ORFS. Table 1 presents correlation coefficients that were determined between certain pairs of these transcript arrays computed with $\log_{10}$ of the expression rations.

TABLE 1

| Row | First Transcript Array | Second Transcript Array | Corr. Coef. | Std. Dev. |
|---|---|---|---|---|
| 1 | wild-type FK506 drug | wild-type CSA drug | 0.334 | 20.9 |
| 2 | wild-type FK506 drug | cna mutant | 0.605 | 37.8 |
| 3 | wild-type FK506 drug | cna mutant, FK506 drug | 0.065 | 4.1 |
| 4 | wild-type FK506 drug | cph1 mutant, FK506 drug | 0.767 | 47.9 |
| 5 | wild-type FK506 drug | fpr1 mutant, FK506 drug | −0.085 | −2.2 |
| 6 | wild-type CSA drug | cna mutant | 0.528 | 33.0 |
| 7 | wild-type CSA drug | cna mutant, CSA drug | 0.028 | 1.8 |
| 8 | wild-type CSA drug | cph1 mutant, CSA drug | 0.154 | 9.6 |
| 9 | wild-type CSA drug | fpr1 mutant, CSA drug | 0.33 | 20.6 |

TABLE 1-continued

| Row | First Transcript Array | Second Transcript Array | Corr. Coef. | Std. Dev. |
|---|---|---|---|---|
| 10 | wild-type FK506 drug | fpr1 mutant | −0.011 | |
| 11 | wild-type CSA drug | cph1 mutant | −0.122 | |
| | 1 Gaussian std. dev. = 0. 016 | | | |

In this table, columns two and three list the transcript arrays that are compared (labeled "First Transcript Array" and "Second Transcript Array"). Their correlation coefficient is presented in the fourth column (labeled "Corr. Coef."). The number of standard deviations represented by the correlation coefficient (in terms of the expected correlation coefficient representing one Gaussian standard deviation) is presented in the fifth column (labeled "Std. Dev."). The expected standard deviation depends on the data set size according to known statistical procedures. The number of standard deviations above the expected mean can be used to determine the statistical significance of the correlation coefficient, as is known in the art.

General Comparisons

The following general conclusions were made concerning the wild-type FK506 and CSA drug transcript arrays and the cna mutant transcript array. Generally, it was observed in the cna mutant transcript array that approximately 2% of the genes were differentially expressed greater than 2-fold. Approximately, the same number of genes displaying differential gene expression was observed in the wild-type FK506 and CSA drug transcript arrays. Visual comparisons of pseudo-color images generated from the transcript array data revealed a large number of genes which were similarly perturbed in the cna mutant transcript arrays and the wild-type drug transcript arrays.

A graphical representation of the similarity of the perturbations induced by the cna deletion mutant on one hand and by the CSA drug treatments on the other is illustrated in FIG. 6. Those ORFs expressed at levels significantly above background were identified in the respective transcript array, and the $\log_{10}$ of the expression ratios of each such ORF were plotted on the Y-axis for the cna deletion mutant cells and on the X-axis for the CSA exposed cells on the X-axis. Genes which were perturbed in the same way (activated, inhibited, or unaffected) to the same extent in both experiments are expected to fall on or near the diagonal. One of skill in the art can appreciate from the substantially oval distribution of the plotted expression ratios aligned along the diagonal that these two perturbations were similar.

In more detail, the correlation coefficient between the cna mutant transcript array and the wild-type CSA drug transcript array was 0.528 (line 6 of Table 1). Since one Gaussian standard deviation was determined to be 0.016, the probability of obtaining a correlation coefficient this large is minute. This indicated that the cna deletion and the CSA drug exposure elicited numerous similar effects on transcript levels resulting in transcript arrays whose similarity was highly statistically significant. Similarly, since the correlation coefficient between the cna mutant transcript array and the FK506 drug transcript array was 0.605 (line 2 of table 1), the results of FK506 treatment were also extremely similar to the results of cna genetic disruption.

It was also observed that not only were the wild-type FK506 and CSA drug transcript arrays individually similar to the cna mutant transcript array, but also both wild-type drug transcript arrays were similar to each other. The correlation coefficient between the two wild-type drug transcript arrays was determined to be 0.334 (line 1 of Table 1).

Thus, it was concluded that the drug-treated wild-type cells are similar and are substantially phenocopies of genetic mutants, since pharmacological inhibition of calcineurin mimicked the genetic deletion in a manner that was highly statistically significant. Although one of skill in the art might have thereby concluded that these two drugs operate by substantially similar mechanisms, application of the further methods of this invention proved FK506 and CSA acted differently.

Drug Target Identification

The methods of this invention were applied in the following manners to identify targets of FK506 and CSA, both primary targets responsible for the primary immunosuppressive effects of these drugs and other targets perhaps responsible for side-effects of these drugs. Concerning primary targets, the following observations were made.

Comparison of the wild-type drug transcript array to the cph1 mutant FK506 drug transcript array revealed a high level of similarity (line 4, see Table 1), indicating that FK506 was able to elicit its characteristic effect in this genetic background (i.e., few sites dropped out due to cph 1 mutation). Conversely, comparison of the wild-type FK506 drug transcript array to the cna mutant FK506 drug transcript array (line 3 of table 1) or fpr1 mutant FK506 drug transcript array (line 5 of table 1) showed that these arrays are not similar, indicating that the perturbations elicited by FK506 were largely blocked by the cna and fpr1 mutations. In other words, most of the FK506 signature "dropped out" due to the cna or fpr1 mutations. Thus, fpr1 and cna were potential FK506 targets, based on the observation that many of the wild-type drug effects dropped out when those mutants were exposed to the drug. (According to the usage herein, the products of the fpr1 and cna genes are also referred to as potential targets of FK506.)

The same set of mutant cells was exposed to CSA treatment. A high degree of statistical similarity was observed between the wild-type CSA drug transcript array and the fpr1 mutant CSA drug transcript array, indicating these this mutation does not affect pathways or processes affected by CSA (line 9 in Table 1) (i.e., few site dropped out due to fpr 1 mutation). A low correlation coefficient was found between the wild-type CSA drug transcript array and the cna mutant CSA drug transcript array (line 7 in Table 1) and the cph1 mutant CSA drug transcript array (line 8 in Table 1). In other words, most of the CSA signature "dropped out" due to the cna or cph1 mutations. Thus, cph1 and cna were potential CSA targets, based on the observation that many of the wild-type drug effects dropped out when those mutants were exposed to the drug. (Also according to the usage herein, the products of the cph1 and cna genes are also referred to as potential targets of CSA.)

The methods of this invention correctly identified the cph1 gene as being a potential target of CSA but not FK506, and the fpr1 gene as being a potential target of FK506 but not of CSA. The mere observation that the wild-type FK506 and CSA drug transcript arrays were similar to the cna mutant transcript array and also similar to each other, by itself, might have suggested to one of skill in the art that FK506 and CSA acted on similar targets. But because the fpr1 mutant FK506 drug transcript array itself did not bear an overall similarity to the wild-type FK506 drug transcript array, the methods of this invention identified fpr1, but not cph1, as a potential FK506 drug target. Similarly, the methods of this invention identified cph1, but not fpr1, as a potential drug target for CSA.

Concerning other targets of CSA and FK506, the following observations were made. Genes for other targets were sought in the database of transcript arrays which were perturbed by a drug treatment of wild-type cells that remained after deletion of an identified primary drug target. For example, for FK506, genes were sought that remained perturbed ("remaining" genes) in the fpr1 mutant FK506 drug transcript array or in the cna mutant FK506 drug transcript array, and for CSA, genes were sought that remained perturbed ("remaining" genes) in the cph1 mutant CSA drug transcript array or in the cna mutant CSA drug transcript array. For CSA, genes were sought that remained perturbed ("remaining" genes) in the cph1 mutant CS drug transcript array or in the cna mutant CSA drug transcript array.

In the case of FK506, three such genes were found which all were perturbed in both the wild-type FK506 transcript array and the cna mutant FK506 drug transcript array. This suggested the expression of these genes is effected by a non-calcineurin FK506 target.

In the case of CSA, analysis of the data found 46 such genes that were likely perturbed in both the wild-type CSA transcript array and the cna mutant CSA drug transcript array. This suggests that there are more non-calcineurin dependent effects on gene transcript levels in CSA exposed cells than in FK506 exposed cells at the concentrations used in this experiment.

6.6.4 Targets of Cyclosporin and FK506

In this example, this invention is used to verify that cna and fpr1 are targets of the drug FK506. The transcript arrays measured in Tables 1 and 2 were similarly produced by the previously described methods.

TABLE 2

| Row | First Transcript Array | Second Transcript Array | Corr. Coef. | Std. Dev. | Corr. Exp. |
|---|---|---|---|---|---|
| 1 | wild-type FK506 drug | cna mutant | 0.245 | 19.4 | Y |
| 2 | wild-type FK506 drug | cna mutant, FK506 drug | 0.052 | 4.1 | N |
| 3 | wild-type FK506 drug | cph1 mutant, FK506 drug | 0.328 | 25.7 | Y |
| 4 | wild-type FK506 drug | fpr1 mutant, FK506 drug | 0.136 | 10.8 | N |
| 5 | wild-type FK506 drug | wild-type CSA drug | 0.243 | 19.6 | Y |

1 Gaussian std. dev. = 0.013
95% confidence limit = 0.026

(This table has columns similar to Table 1, except in that a sixth column (labeled "Corr. Exp.") indicated whether a correlation is expected in view of the drug target interpretation presented in the accompanying text, which was developed in view of all the correlation data.)

The identification of the cna and fpr1 genes (or, equivalently, of their gene products) as targets of FK506 were determined as illustrated in Table 2. The correlation coefficient between the wild-type FK506 drug transcript array and the cna deletion transcript array was determined to be 0.245, indicating, in view of the standard deviation of 19.4, a high level of similarity between the two transcript arrays (row 1 of Table 2). (Correlation coefficients observed in different experiments are not necessarily directly numerically comparable, because sample sizes in the experiments can differ sufficiently.) The correlation coefficient, coupled with the standard deviation (which is dependent on sample size), was used to calculate a likelihood that this observed similarity was due to chance. The likelihood that these two transcript arrays were similar due to chance alone was extremely remote.

The correlation coefficient between the wild-type FK506 drug transcript array and the cna deletion FK506 drug transcript array was determined to be 0.052 with a standard deviation of only 4.1, indicating that these two transcript arrays are not highly similar (row 2 of Table 2). Most of the drug effects of FK506 dropped out due to the cna deletion. (Genes remaining in the cna deletion FK506 drug transcript array, of course, correlated with the same genes in the wild-type FK506 drug transcript array.) The likelihood that these two transcript arrays were dissimilar due to chance alone was extremely remote.

The correlation coefficient between the wild-type FK506 drug transcript array and the cph1 mutant FK506 drug transcript array was determined to be 0.328, indicating, in view of the standard deviation of 25.7, a high level of similarity between the two transcript arrays (row 3 of Table 2). Most of the effects of FK506 remained after the cph1 mutation. The likelihood that these two transcript arrays were similar due to chance alone was extremely remote.

Finally, the correlation coefficient between the wild-type FK506 drug transcript array and the fpr1 deletion FK506 drug transcript array was determined to be 0.136 with a standard deviation of 10.8, indicating that these two transcript arrays are not substantially similar (row 4 of Table 2). Many of the drug effects of FK506 dropped out due to the fpr1 deletion (which encodes one of four FKBPs). The likelihood that these two transcript arrays were dissimilar due to chance alone was small.

These results indicated, first, that a large number of genes were similarly affected in the cna mutant transcript arrays and the wild-type FK506 transcript arrays. Second, these results indicated that the cna and fpr1 genes fundamentally affected how the cell responds to FK506. Third, the cph1 gene did not appear to affect how the cell responds to FK506.

In summary, these results indicated that cna and fpr1 were targets for FK506, whereas cph1 was not a target for FK506.

Further independent data concerning CSA and FK506 and the cna, cph1, and fpr1 deletion mutants is presented in Table 3. This table, in contrast to Table 1 and 2 (which were created from microarrays with approximately 5900 ORF sites) was created from microarray having sites with 140 *S. cerevisiae* selected ORF sites thought to be relevant to the primary action of these drugs. Correlation coefficients were computed using $\log_{10}$ of the raw expression ratios.

TABLE 3

| Row | First Transcript Array | Second Transcript Array | Corr. Coef. | Std. Dev. | Corr. Exp. |
|---|---|---|---|---|---|
| 1 | Wild-type FK506 drug | cna mutant | 0.61 | 6.4 | Y |
| 2 | Wild-type FK506 drug | cna mutant, FK506 drug | -0.12 | -1.3 | N |

TABLE 3-continued

| Row | First Transcript Array | Second Transcript Array | Corr. Coef. | Std. Dev. | Corr. Exp. |
|---|---|---|---|---|---|
| 3 | Wild-type FK506 drug | cph1 mutant, FK506 drug | 0.70 | 7.3 | Y |
| 4 | Wild-type FK506 drug | fpr1 mutant, FK506 drug | 0.04 | 0.4 | N |
| 5 | Wild-type CSA drug | cna mutant | 0.76 | 8.6 | Y |
| 6 | Wild-type CSA drug | cna mutant, CSA drug | 0.15 | 1.7 | N |
| 7 | Wild-type CSA drug | cph1 mutant, CSA drug | 0.32 | 3.5 | N |
| 8 | Wild-type CSA drug | fpr1 mutant, CSA drug | 0.63 | 6.9 | Y |
| 9 | Wild-type FK506 drug | Wild-type CSA drug | 0.67 | 6.9 | Y |
| 10 | Wild-type vs wild-type | cna mutant | 0.01 | 0.1 | N |
| 11 | Wild-type vs wild-type | cph1 mutant | 0.04 | 0.4 | N |
| 12 | Wild-type vs wild-type | fpr1 mutant | 0.18 | 1.9 | N |
| 13 | Wild-type vs wild-type | Wild-type FK506 drug | −0.05 | −0.5 | N |
| 14 | Wild-type vs wild-type | Wild-type CSA drug | 0.04 | 0.4 | N |
| 15 | cna mutant, FK506 drug | cna mutant, CSA drug | 0.20 | 2.2 | N |
| 16 | cph1 mutant, FK506 drug | cph1 mutant, CSA drug | 0.15 | 1.7 | N |
| 17 | fpr1 mutant, FK506 drug | fpr1 mutant, CSA drug | −0.01 | −0.2 | N |
| 18 | cph1 mutant, FK506 drug | fpr1 mutant, CSA drug | 0.71 | 7.3 | Y |
| 19 | fpr1 mutant, FK506 drug | cph1 mutant, CSA drug | 0.40 | 4.4 | N |

1 Gaussian std. dev. = 0.09
95% confidence limit = 0.19

(Table 3 has columns similar to Table 2.)

The data of rows 1–9 recapitulates data leading to the previous conclusions found from corresponding data in Tables 1 and 2.

Rows 10–14 provide negative control data in which the absence of significant correlation reflects the absence of systematic experimental biases. The wild-type cell vs. wild-type cell transcript array was a control experiment in which cells in the same condition, without gene deletions or drug exposures, were compared to themselves. Such a transcript array is expected to reflect any random effects (noise) present in the experimental arrangement. In the other transcript arrays in these correlations, wild-type cells were compared to cells in which there was either gene deletion or drug exposure. Some degree of correlation between these two types of transcript arrays would be expected only in the presence of systematic experimental biases that would tend to cause similar perturbations at corresponding sites in transcript arrays regardless of varying treatments. In the absence of such experimental bias, there is no expectation that the effects of deletion mutants or drug exposure would correlate to a null control experiment reflecting random experimental noise. The absence of significant correlation in these cases demonstrated an absence of significant systematic experimental bias affecting the reported results.

No correlation is expected in rows 15 and 19 because the two transcript arrays correlated reflect the presumably independent effects of two different drugs in cells with a primary target for one of the drugs disrupted (i.e., presumably independent secondary targets are being compared). (However, the correlation observed in row 19 is higher than expected.)

No correlation is expected in rows 16 and 17 because, in one of the transcript arrays being correlated here, no drug effect is expected in view of disruption of a primary target, and, in the other transcript array being correlated here, a drug effect is expected in view of a lack of disruption of a primary target.

A correlation is expected in row 18 since the two transcript arrays correlated reflect the effects of drugs with similar effect in cells disrupted for genes involved in pathways unrelated to the pathway presumably affected by the drugs.

Where no correlation was expected, strong correlation was not observed (except for row 19).

7 REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of determining that a putative drug target is an actual drug target comprising:
    (a) identifying genes or gene products whose abundances are changed in a cell of said cell type that is exposed to said drug in comparison to a cell of said cell type that is not exposed to said drug;
    (b) identifying genes or gene products whose abundances are changed in a cell of said cell type that has said putative drug target modified in comparison to a cell of said cell type that does not have said putative drug target modified; and
    (c) ascertaining if each said gene or gene product identified in step (a) is also identified in step (b), and
    (d) determining said putative drug target as an actual drug target if each said gene or gene product identified in step (a) is also identified in step (b).

2. The method of claim 1 wherein said genes or gene products comprise a plurality of RNA species present in said cell type.

3. The method of claim 2 wherein the abundances of said plurality of RNA species are measured by a method comprising contacting a gene transcript array with RNA from a cell of said cell type, or with cDNA derived therefrom, wherein a gene transcript array comprises a surface with attached nucleic acids or nucleic acid mimics, said nucleic acids or nucleic acid mimics capable of hybridizing with said plurality of RNA species, or with cDNA derived therefrom.

4. The method of claim 1 wherein said identifying genes or gene products whose abundances are changed in step (a) is performed by a method comprising contacting one or more gene transcript arrays with RNA, or with cDNA derived therefrom, from said cell of said cell type that is exposed to said drug and with RNA, or with cDNA derived therefrom, from said cell of said cell type that is not exposed to said drug, and wherein said identifying genes or gene products whose abundances are changed in step (b) is performed by a method comprising contacting one or more gene transcript arrays with RNA, or with cDNA derived therefrom, from said cell of said cell type that has said putative drug target modified and with RNA, or with cDNA derived therefrom, from said cell of said cell type that does not have said putative drug target modified.

5. The method of claim 1 wherein said genes or gene products whose abundances are changed comprise a plurality of protein species present in said cell type.

6. The method of claim 5 wherein the abundances of said plurality of protein species are measured by a method comprising contacting an antibody array with proteins from a cell of said cell type, wherein said antibody array comprises a surface with attached antibodies, said antibodies capable of binding with said plurality of protein species.

7. The method of claim 1 wherein the abundances of said plurality of protein species are measured by a method comprising performing two dimensional electrophoresis of proteins from a cell of said cell type.

8. The method of claim 1 wherein said putative drug target is modified by a method comprising disrupting a gene encoding said putative drug target in a cell of said cell type.

9. The method of claim 1 wherein said putative drug target is modified by a method comprising causing overexpression of a gene encoding said putative drug target in a cell of said cell type.

10. The method of claim 1 wherein said putative drug target is modified by a method comprising decreasing the abundance of an RNA species encoding said putative drug target in a cell of said cell type.

11. The method of claim 10 wherein said method of decreasing the abundance of an RNA species comprises exposing a cell of said cell type to a ribozyme targeting and cleaving said RNA species.

12. The method of claim 1 wherein said putative drug target is modified by a method comprising decreasing the rate of translation of an RNA species encoding said putative drug target in a cell of said cell type.

13. The method of claim 12 wherein said method of decreasing the rate of translation of an RNA species comprises exposing a cell of said cell type to an antisense nucleic acid or antisense nucleic acid mimic that hybridizes to said RNA species or to DNA encoding said RNA species.

14. The method of claim 1 wherein said putative drug target is a protein species, and wherein said putative drug target is modified by a method comprising decreasing the abundance of said protein species in a cell of said cell type.

15. The method of claim 14 wherein said method of decreasing the abundance comprises causing expression in a cell of said cell type of said protein species as a fusion protein comprising said protein species and a degron, wherein said degron is inducible to increase the rate of degradation of said protein species.

16. The method of claim 14 wherein said method of decreasing the abundance comprises exposing a cell of said cell type to an antibody, wherein said antibody binds said protein species.

17. The method of claim 1 wherein said putative drug target is an activity of a protein species, and wherein said putative drug target is modified by a method comprising decreasing said activity in a cell of said cell type.

18. The method of claim 17 wherein said method of decreasing the activity comprises exposing a cell of said cell type to a drug which directly inhibits said activity of said protein species.

19. The method of claim 17 wherein said method of decreasing the activity comprises exposing a cell of said cell type to a dominant negative mutant protein species, wherein said dominant negative mutant protein species is a protein inhibiting said activity.

20. The method of claim 1 wherein step (c) further ascertains whether abundance of each said gene or gene product is changed similarly in step (a) and in step (b).

21. A method of determining whether a putative target of a drug is an actual target of said drug, comprising comparing a first pattern and a second pattern, wherein said first pattern comprises changes in abundances of a plurality of cellular constituents in a wild-type cell exposed to said drug versus in a wild-type cell not exposed to said drug, wherein said second pattern comprises changes in abundances of said plurality of cellular constituents in a modified cell versus in a wild-type cell, said modified cell being a cell comprising a modification to said putative drug target as compared to said wild-type cell, and wherein a high similarity between said first pattern and said second pattern indicates that said putative target of said drug is an actual target of said drug.

22. The method of claim 21, further comprising obtaining said first pattern and said second pattern.

23. The method of claim 22, wherein said comparing is carried out by a method comprising determining a correlation coefficient between said first pattern and said second pattern.

24. The method of claim 23, wherein said putative drug target is a gene or gene product.

25. The method of claim 24, wherein said gene or gene product is modified by a method comprising disrupting the expression of said gene in a cell of said cell type.

26. The method of claim 24, wherein said gene or gene product is a protein, and wherein said modified cell is obtained by a method comprising decreasing abundance of said protein or decreasing activity of said protein in said modified cell.

27. The method of claim 21, wherein said plurality of cellular constituents comprises a plurality of gene transcripts.

* * * * *